US009409029B2

(12) United States Patent
Perryman et al.

(10) Patent No.: US 9,409,029 B2
(45) Date of Patent: Aug. 9, 2016

(54) REMOTE RF POWER SYSTEM WITH LOW PROFILE TRANSMITTING ANTENNA

(71) Applicant: Micron Devices LLC, Miami Beach, FL (US)

(72) Inventors: Laura Tyler Perryman, Miami Beach, FL (US); Richard LeBaron, Miami Beach, FL (US); Andrej Simeunovic, Miami Beach, FL (US)

(73) Assignee: Micron Devices LLC, Miami Beach, FL (US)

( * ) Notice: Subject to any disclaimer, the term of this patent is extended or adjusted under 35 U.S.C. 154(b) by 0 days.

(21) Appl. No.: 14/710,548

(22) Filed: May 12, 2015

(65) Prior Publication Data

US 2015/0321017 A1 Nov. 12, 2015

Related U.S. Application Data

(60) Provisional application No. 61/992,150, filed on May 12, 2014.

(51) Int. Cl.
*A61N 1/00* (2006.01)
*A61N 1/372* (2006.01)
*H01Q 9/26* (2006.01)
(Continued)

(52) U.S. Cl.
CPC .......... *A61N 1/37229* (2013.01); *A61N 1/3605* (2013.01); *A61N 1/3787* (2013.01); *H01Q 9/26* (2013.01); *H01Q 13/00* (2013.01)

(58) Field of Classification Search
CPC ............ A61N 1/3605; A61N 1/37229; A61N 1/3787; H01Q 13/00; H01Q 9/26
See application file for complete search history.

(56) References Cited

U.S. PATENT DOCUMENTS 2,990,547 A 6/1961 McDougal
3,662,758 A 5/1972 Glover
(Continued)

FOREIGN PATENT DOCUMENTS

CN 1678370 10/2005
CN 101185789 5/2008
(Continued)

OTHER PUBLICATIONS

US 5,197,469, 3/1993, Adams (withdrawn).
(Continued)

*Primary Examiner* — George Manuel
(74) *Attorney, Agent, or Firm* — Fish & Richardson P.C.

(57) ABSTRACT

An antenna assembly includes: an antenna including: a metal signal layer having a radiating surface; and a feed port; and a waveguide surrounding the antenna and configured to guide electromagnetic energy transmitted from the radiating surface in a direction away from the antenna; and a controller module connected to the feed port and configured to drive the antenna to transmit electromagnetic energy from the radiating surface; wherein the antenna, waveguide, and controller module are configured such that, when the controller module drives the antenna, the transmitted electromagnetic energy matches a reception characteristic of an implantable device and is sufficient for the implantable device to create one or more electrical pulses of sufficient amplitude to stimulate neural tissue of a patient, solely using electromagnetic energy received from the antenna, when the implantable device is located at least 10 centimeters away from the antenna.

28 Claims, 19 Drawing Sheets

(51) Int. Cl.
*H01Q 13/00* (2006.01)
*A61N 1/36* (2006.01)
*A61N 1/378* (2006.01)

(56) References Cited

U.S. PATENT DOCUMENTS

| | | | |
|---|---|---|---|
| 3,663,758 A | 5/1972 | Erbert | |
| 3,727,616 A | 4/1973 | Lenzkes | |
| 4,057,069 A | 11/1977 | Dorffer et al. | |
| 4,102,344 A | 7/1978 | Conway et al. | |
| 4,494,950 A | 1/1985 | Fischell | |
| 4,524,774 A | 6/1985 | Hildebrandt | |
| 4,525,774 A | 6/1985 | Kino et al. | |
| 4,561,443 A | 12/1985 | Hogrefe et al. | |
| 4,592,359 A | 6/1986 | Galbraith | |
| 4,612,934 A | 9/1986 | Borkan | |
| 4,628,933 A | 12/1986 | Michelson | |
| 4,736,752 A | 4/1988 | Munck | |
| 4,741,339 A | 5/1988 | Harrison et al. | |
| 4,750,499 A | 6/1988 | Hoffer | |
| 4,793,353 A | 12/1988 | Borkan | |
| 4,837,049 A | 6/1989 | Byers et al. | |
| 4,947,844 A | 8/1990 | McDermott | |
| 5,058,581 A | 10/1991 | Silvian | |
| 5,070,535 A | 12/1991 | Hochmair et al. | |
| 5,193,539 A | 3/1993 | Schulman et al. | |
| 5,262,793 A | 11/1993 | Sperry | |
| 5,314,458 A | 5/1994 | Najafi et al. | |
| 5,343,766 A | 9/1994 | Lee | |
| 5,358,514 A | 10/1994 | Schulman et al. | |
| 5,411,535 A | 5/1995 | Fujii et al. | |
| 5,583,510 A | 12/1996 | Ponnapalli et al. | |
| 5,591,217 A | 1/1997 | Barreras | |
| 5,626,630 A | 5/1997 | Markowitz et al. | |
| 5,735,887 A | 4/1998 | Barreras, Sr. et al. | |
| 5,769,877 A | 6/1998 | Barreras | |
| 5,861,019 A | 1/1999 | Sun et al. | |
| 5,991,664 A | 11/1999 | Seligman | |
| 5,995,874 A | 11/1999 | Borza | |
| 6,141,588 A | 10/2000 | Cox et al. | |
| 6,175,752 B1 | 1/2001 | Say et al. | |
| 6,350,335 B1 | 2/2002 | Hampel et al. | |
| 6,415,184 B1 | 7/2002 | Ishikawa et al. | |
| 6,445,953 B1 | 9/2002 | Bulkes et al. | |
| 6,445,955 B1 | 9/2002 | Michelson et al. | |
| 6,458,157 B1 | 10/2002 | Suaning | |
| 6,463,336 B1 | 10/2002 | Mawhinney | |
| D466,487 S | 12/2002 | Wada et al. | |
| 6,516,227 B1 | 2/2003 | Meadows et al. | |
| D474,982 S | 5/2003 | Wilson | |
| 6,564,807 B1 | 5/2003 | Schulman et al. | |
| 6,611,715 B1 | 8/2003 | Boveja | |
| 6,615,081 B1 | 9/2003 | Boveja | |
| 6,647,296 B2 | 11/2003 | Fischell et al. | |
| 6,662,052 B1 | 12/2003 | Sarwal et al. | |
| 6,684,104 B2 | 1/2004 | Gordon et al. | |
| 6,690,974 B2 | 2/2004 | Archer et al. | |
| 6,889,086 B2 | 5/2005 | Mass et al. | |
| 6,895,280 B2 | 5/2005 | Meadows et al. | |
| 6,972,727 B1 * | 12/2005 | West et al. | 343/771 |
| 7,027,874 B1 | 4/2006 | Sawan et al. | |
| 7,110,823 B2 | 9/2006 | Whitehurst et al. | |
| D529,402 S | 10/2006 | Burton | |
| 7,177,690 B2 | 2/2007 | Woods et al. | |
| 7,214,189 B2 | 5/2007 | Zdeblick | |
| 7,277,728 B1 | 10/2007 | Kauhanen | |
| 7,283,875 B2 | 10/2007 | Larsson | |
| 7,317,947 B2 | 1/2008 | Wahlstrand et al. | |
| 7,436,752 B2 | 10/2008 | He | |
| 7,471,257 B2 | 12/2008 | Candal et al. | |
| 7,489,248 B2 | 2/2009 | Gengel et al. | |
| 7,616,991 B2 * | 11/2009 | Mann et al. | 607/9 |
| 7,620,451 B2 | 11/2009 | Demarais | |
| 7,630,771 B2 | 12/2009 | Cauller | |
| 7,664,552 B2 | 2/2010 | Wahlstrand et al. | |
| D612,543 S | 3/2010 | Marseille | |
| 7,738,964 B2 | 6/2010 | Von Arx et al. | |
| 7,741,734 B2 | 6/2010 | Joannopoulos et al. | |
| 7,765,013 B2 | 7/2010 | Blick et al. | |
| 7,853,333 B2 | 12/2010 | Demarais | |
| 7,869,885 B2 | 1/2011 | Begnaud et al. | |
| 7,894,905 B2 | 2/2011 | Pless et al. | |
| 7,904,170 B2 | 3/2011 | Harding | |
| 7,908,014 B2 | 3/2011 | Schulman et al. | |
| 7,939,346 B2 | 5/2011 | Blick et al. | |
| D658,302 S | 4/2012 | Nixon | |
| 8,170,672 B2 | 5/2012 | Weiss et al. | |
| 8,242,968 B2 | 8/2012 | Conrad et al. | |
| 8,320,850 B1 | 11/2012 | Khlat | |
| 8,332,040 B1 | 12/2012 | Winstrom | |
| D701,504 S | 3/2014 | Christopher et al. | |
| D703,204 S | 4/2014 | Riddiford et al. | |
| D714,288 S | 9/2014 | Aumiller et al. | |
| 8,849,412 B2 | 9/2014 | Perryman et al. | |
| 8,903,502 B2 | 12/2014 | Perryman et al. | |
| D721,701 S | 1/2015 | Al-Nasser | |
| D725,071 S | 3/2015 | Lee et al. | |
| D725,072 S | 3/2015 | Kim et al. | |
| D725,652 S | 3/2015 | Ishii | |
| D734,330 S | 7/2015 | Huang et al. | |
| 9,199,089 B2 | 12/2015 | Perryman et al. | |
| 9,220,897 B2 | 12/2015 | Perryman et al. | |
| 9,242,103 B2 | 1/2016 | Perryman et al. | |
| 9,254,393 B2 | 2/2016 | Perryman et al. | |
| 2001/0010662 A1 | 8/2001 | Saitou et al. | |
| 2003/0114898 A1 | 6/2003 | Von Arx et al. | |
| 2003/0114899 A1 | 6/2003 | Woods et al. | |
| 2003/0139782 A1 | 7/2003 | Duncan et al. | |
| 2003/0169207 A1 | 9/2003 | Beigel | |
| 2003/0204224 A1 | 10/2003 | Torgerson et al. | |
| 2004/0059392 A1 | 3/2004 | Parramon et al. | |
| 2004/0082979 A1 | 4/2004 | Tong et al. | |
| 2004/0127942 A1 | 7/2004 | Yomtov et al. | |
| 2004/0138723 A1 | 7/2004 | Malick et al. | |
| 2004/0167587 A1 | 8/2004 | Thompson | |
| 2004/0176803 A1 | 9/2004 | Whelan et al. | |
| 2004/0220621 A1 | 11/2004 | Zhou | |
| 2004/0230263 A1 | 11/2004 | Samulski | |
| 2005/0119716 A1 | 6/2005 | McClure et al. | |
| 2005/0137668 A1 | 6/2005 | Khan | |
| 2005/0245994 A1 | 11/2005 | Varrichio et al. | |
| 2006/0001583 A1 | 1/2006 | Bisig | |
| 2006/0003721 A1 | 1/2006 | Bisig | |
| 2006/0085039 A1 | 4/2006 | Hastings et al. | |
| 2006/0085042 A1 | 4/2006 | Hastings et al. | |
| 2006/0161225 A1 | 7/2006 | Sormann et al. | |
| 2006/0287686 A1 | 12/2006 | Cullen et al. | |
| 2006/0289528 A1 | 12/2006 | Chiu et al. | |
| 2007/0055324 A1 | 3/2007 | Thompson et al. | |
| 2007/0100395 A1 | 5/2007 | Ibrahim | |
| 2007/0100935 A1 | 5/2007 | Miyazaki et al. | |
| 2007/0106337 A1 | 5/2007 | Errico et al. | |
| 2007/0109208 A1 | 5/2007 | Turner | |
| 2007/0112402 A1 | 5/2007 | Grill et al. | |
| 2007/0156179 A1 | 7/2007 | S.E. | |
| 2007/0213773 A1 | 9/2007 | Hill et al. | |
| 2007/0213783 A1 | 9/2007 | Pless | |
| 2007/0254632 A1 | 11/2007 | Beadle et al. | |
| 2007/0265543 A1 | 11/2007 | VanSickle et al. | |
| 2007/0265690 A1 | 11/2007 | Lichtenstein et al. | |
| 2007/0288066 A1 | 12/2007 | Christman et al. | |
| 2008/0010358 A1 | 1/2008 | Jin | |
| 2008/0046012 A1 | 2/2008 | Covalin et al. | |
| 2008/0077184 A1 | 3/2008 | Denker et al. | |
| 2008/0077188 A1 | 3/2008 | Denker et al. | |
| 2008/0266123 A1 | 10/2008 | Ales et al. | |
| 2008/0281244 A1 | 11/2008 | Jacobs | |
| 2009/0018599 A1 | 1/2009 | Hastings et al. | |
| 2009/0099405 A1 | 4/2009 | Schneider et al. | |
| 2009/0105784 A1 | 4/2009 | Massoud-Ansari | |
| 2009/0125091 A1 * | 5/2009 | Schoenbach et al. | 607/156 |
| 2009/0132002 A1 | 5/2009 | Kieval | |
| 2009/0132003 A1 | 5/2009 | Borgens et al. | |
| 2009/0200985 A1 | 8/2009 | Zane et al. | |

(56) References Cited

U.S. PATENT DOCUMENTS

| | | | |
|---|---|---|---|
| 2009/0204170 A1 | 8/2009 | Hastings et al. |
| 2009/0234407 A1 | 9/2009 | Hastings et al. |
| 2009/0248112 A1 | 10/2009 | Mumbru et al. |
| 2010/0053789 A1 | 3/2010 | Duric et al. |
| 2010/0114198 A1 | 5/2010 | Donofrio et al. |
| 2010/0125269 A1 | 5/2010 | Emmons et al. |
| 2010/0137938 A1 | 6/2010 | Kishawi et al. |
| 2010/0168818 A1 | 7/2010 | Barror et al. |
| 2010/0174340 A1 | 7/2010 | Simon |
| 2010/0179449 A1 | 7/2010 | Chow et al. |
| 2010/0198039 A1 | 8/2010 | Towe |
| 2010/0198307 A1 | 8/2010 | Toy et al. |
| 2010/0231382 A1 | 9/2010 | Tayrani et al. |
| 2010/0234922 A1 | 9/2010 | Forsell |
| 2010/0268298 A1 | 10/2010 | Moffitt et al. |
| 2010/0298742 A1 | 11/2010 | Perlman et al. |
| 2010/0331934 A1 | 12/2010 | McDonald et al. |
| 2011/0040350 A1 | 2/2011 | Griffith |
| 2011/0074342 A1 | 3/2011 | MacLaughlin |
| 2011/0077698 A1 | 3/2011 | Tsampazis et al. |
| 2011/0098583 A1 | 4/2011 | Pandia et al. |
| 2011/0106220 A1 | 5/2011 | DeGiorgio et al. |
| 2011/0120822 A1 | 5/2011 | Kondou et al. |
| 2011/0121822 A1 | 5/2011 | Parsche |
| 2011/0125214 A1 | 5/2011 | Goetz et al. |
| 2011/0130804 A1 | 6/2011 | Lin et al. |
| 2011/0144468 A1 | 6/2011 | Boggs et al. |
| 2011/0172733 A1 | 7/2011 | Lima et al. |
| 2011/0190849 A1 | 8/2011 | Faltys et al. |
| 2011/0245892 A1 | 10/2011 | Kast et al. |
| 2012/0004709 A1 | 1/2012 | Chen et al. |
| 2012/0158407 A1 | 6/2012 | Forsell |
| 2012/0194399 A1 | 8/2012 | Bily et al. |
| 2012/0215218 A1 | 8/2012 | Lipani |
| 2012/0283800 A1 | 11/2012 | Perryman et al. |
| 2013/0016016 A1 | 1/2013 | Lin et al. |
| 2013/0018439 A1 | 1/2013 | Chow et al. |
| 2013/0165991 A1 | 6/2013 | Kim |
| 2014/0058480 A1 | 2/2014 | Perryman et al. |
| 2014/0058481 A1 | 2/2014 | Perryman et al. |
| 2014/0169142 A1 | 6/2014 | Heck et al. |
| 2014/0266935 A1 | 9/2014 | Tankiewicz |
| 2014/0336727 A1 | 11/2014 | Perryman et al. |

FOREIGN PATENT DOCUMENTS

| | | |
|---|---|---|
| CN | 101352596 | 1/2009 |
| CN | 101773701 | 7/2010 |
| CN | 201676401 | 12/2010 |
| EP | 1588609 | 10/2005 |
| WO | WO 0013585 | 3/2000 |
| WO | WO 2006113802 | 10/2006 |
| WO | WO 2007059386 | 5/2007 |
| WO | WO 2010051189 | 5/2010 |
| WO | WO 2010053789 | 5/2010 |
| WO | WO 2010104569 | 9/2010 |
| WO | WO 2011079309 | 6/2011 |
| WO | WO 2012103519 | 8/2012 |
| WO | WO 2012138782 | 10/2012 |
| WO | WO 2013019757 | 2/2013 |
| WO | WO 2013025632 | 2/2013 |
| WO | WO 2013040549 | 3/2013 |

OTHER PUBLICATIONS

U.S. Appl. No. 29/478,687, filed Jan. 7, 2014, Perryman et al.
"Assembly, Wearable Antenna, 350-450 MHz," Retrieved from the Internet: <URL: http://www.pharad.com/pdf/UHF-Wearable-Antenna-2D.pdf>, Oct. 14, 2010, 1 page.
"Pharad at Forefront of LTE Antenna Innovation with Development of LTE Wearable Antenna," Wireless Design Mag [online] Aug. 12, 2013. Retrieved from the Internet: <URL: http://www.wirelessdesignmag.com/product-release/2013/08/pharad-forefront-lte-antenna-innovation-development-lte-wearable-antenna>, 3 pages.
Iannetta, "Nov. 2014 New Products: Wearable coil facilitates positioning during prostate MRI" Urology Times [online] Nov. 10, 2014 [retrieved Mar. 17, 2016]. Retrieved from the Internet: <URL: http://urologytimes.modernmedicine.com/urology-times/news/november-2014-new-products-wearable-coil-facilitates-positioning-during-prostate-mri?page=full>, 7 pages.
O'Driscoll et al., "A mm-Sized implantable power receiver with adaptive link compensation," ISSCC 2009, Session 17, TD: Energy-Aware Sensor Systems, 17.5, 2009, 3 pages.
Poon et al., "Optimal frequency for wireless power transmission into dispersive tissue," IEEE Transactions on Antennas and Propagation, May 2010, 58(5):1739-1750.
Extended European Search report in Application No. 12740011.7, dated Sep. 9, 2015, 6 pages.
Extended European Search report in Application No. 12767575.9, dated Nov. 7, 2014, 7 pages.
Extended European Search report in Application No. 12819482.6, dated Apr. 28, 2015, 7 pages.
Extended European Search Report in Application No. 12824347.4, dated Apr. 22, 2015, 6 pages.
Partial Supplementary European Search Report in Application No. 12831083.6, dated Mar. 24, 2015, 7 pages.
Extended European Search report in Application No. 12831083.6, dated Aug. 17, 2015, 9 pages.
Chinese Office Action in Application No. 201280006578.7, dated Jul. 29, 2014, 6 pages.
Chinese Office Action in Application No. 201280006578.7, dated Dec. 8, 2014, 6 pages (with English tmnslation).
Chinese Office Action in Application No. 201280006578.7, dated Mar. 2, 2016, 5 pages.
Chinese Office Action in Application No. 201280017245.4, dated Dec. 3, 2014, 6 pages (with English tmnslation).
Chinese Office Action in Application No. 201280017245.4, dated Aug. 3, 2015, 16 pages (with English translation).
Chinese Office Action in Application No. 201280017245, dated Mar. 2, 2016, 6 pages.
Chinese Office Action in Application No. 201280037814, dated May 6, 2015, 18 pages.
Office action in Chinese Application No. 201280037814.1 mailed Mar. 7, 2016, 13 pages.
U.S. Non-Final Office Action for U.S. Appl. No. 13/551,050 dated Mar. 4, 2014, 30 pages.
U.S. Final Office Action for U.S. Appl. No. 13/551,050, dated Feb. 13, 2015, 18 pages.
U.S. Advisory Action for U.S. Appl. No. 13/551,050, dated Apr. 24, 2015, 3 pages.
U.S. Non-Final Office Action for U.S. Appl. No. 13/551,050 dated Sep. 24, 2015, 16 pages.
U.S. Non-Final Office Action for U.S. Appl. No. 13/562,221, dated Jan. 29, 2014, 30 pages.
U.S. Final Office Action for U.S. Appl. No. 13/562,221, dated Oct. 23, 2014, 22 pages.
U.S. Notice of Allowance for U.S. Appl. No. 13/562,221, mailed Jul. 21, 2015, 8 pages.
U.S. Non-Final Office Action for U.S. Appl. No. 13/584,618 dated Jun. 12, 2013, 15 pages.
U.S. Final Office Action for U.S. Appl. No. 13/584,618, dated Aug. 26, 2013, 13 pages.
U.S. Notice of Allowance for U.S. Appl. No. 13/584,618, dated May 16, 2014, 8 pages.
U.S. Non-Final Office Action for U.S. Appl. No. 13/621,530, dated Apr. 11, 2014, 15 pages.
U.S. Final Office Action for U.S. Appl. No. 13/621,530, dated Jan. 5, 2015, 32 pages.
U.S. Notice of Allowance for U.S. Appl. No. 13/621,530, mailed Aug. 20, 2015, 9 pages.
U.S. Notice of Allowance for U.S. Appl. No. 13/621,530, mailed Oct. 7, 2015, 4 pages.
U.S. Non-Final Office Action for U.S. Appl. No. 13/897,427, dated Jan. 9, 2014, 24 pages.
U.S. Notice of Allowance for U.S. Appl. No. 13/897,427, mailed Jul. 28, 2014, 8 pages.

(56) References Cited

OTHER PUBLICATIONS

U.S. Notice of Allowance for U.S. Appl. No. 13/897,427, mailed Sep. 24, 2014, 4 pages.
U.S. Non-Final Office Action for U.S. Appl. No. 14/045,764 dated Feb. 6, 2015, 14 pages.
U.S. Non-Final Office Action for U.S. Appl. No. 14/045,764 dated Apr. 1, 2015, 15 pages.
U.S. Notice of Allowance for U.S. Appl. No. 14/045,764, mailed Aug. 17, 2015, 11 pages.
U.S. Non-Final Office Action for U.S. Appl. No. 14/068,750 dated Jan. 9, 2015, 27 pages.
U.S. Final Office Action for U.S. Appl. No. 14/068,750 dated Jul. 29, 2015, 13 pages.
U.S. Non-Final Office Action in U.S. Appl. No. 14/068,750, dated Jan. 4, 2016, 13 pages.
U.S. Non-Final Office Action for U.S. Appl. No. 14/141,197, mailed Mar. 4, 2015, 11 pages.
U.S. Final Office Action for U.S. Appl. No. 14/141,197, mailed Jul. 8, 2015, 11 pages.
U.S. Final Office Action in U.S. Appl. No. 14/445,159, dated Dec. 15, 2015, 7 pages.
Office Action in JP Application No. 2013-551396, dated Jan. 12, 2016, 7 pages (with English translations).
U.S. Non-Final Office Action for U.S. Appl. No. 29/478,687, mailed Aug. 12, 2015, 8 pages.
International Search Report and Written Opinion for PCT/US2012/023029, mailed May 16, 2012, 11 pages.
International Preliminary Report on Patentability for PCT/US2012/023029, issued Jan. 28, 2014, 9 pages.
International Search Report and Written Opinion for PCT/US2012/032200, mailed Jul. 27, 2014, 13 pages.
International Preliminary Report on Patentability and Written Opinion for PCT/US2012/032200 issued Oct. 8, 2013, 11 pages.
International Search Report and the Written Opinion for Application No. PCTUS2012048903 dated Oct. 10, 2012, 10 pages.
International Preliminary Report on Patentability and Written Opinion for PCT/US2012/048903, issued Mar. 25, 2014, 8 pages.
International Search Report and Written Opinion of Application No. PCTUS 1250633 dated Oct. 23, 2012, 8 pages.
International Preliminary Report on Patentability issued in International Application No. PCT/US2012/050633, issued Feb. 18, 2014, 7 pages.
International Search Report and PCT Written Opinion of the International Searching Authority for application PCT/US2012/55746, dated Jan. 3, 2013, 11 pages.
International Preliminary Report on Patentability issued in International Application No. PCT/US2012/055746, issued Mar. 18, 2014, 10 pages.
International Search Report and Written Opinion for International Application No. PCT/US2013/077846 dated Apr. 21, 2014, 10 pages.
International Preliminary Report on Patentability for PCT/US2013/077846, issued Jun. 30, 2015, 6 pages.
International Search Report and Written Opinion in International Application No. PCT/US2015/030433, dated Sep. 29, 2015, 18 pages.

* cited by examiner

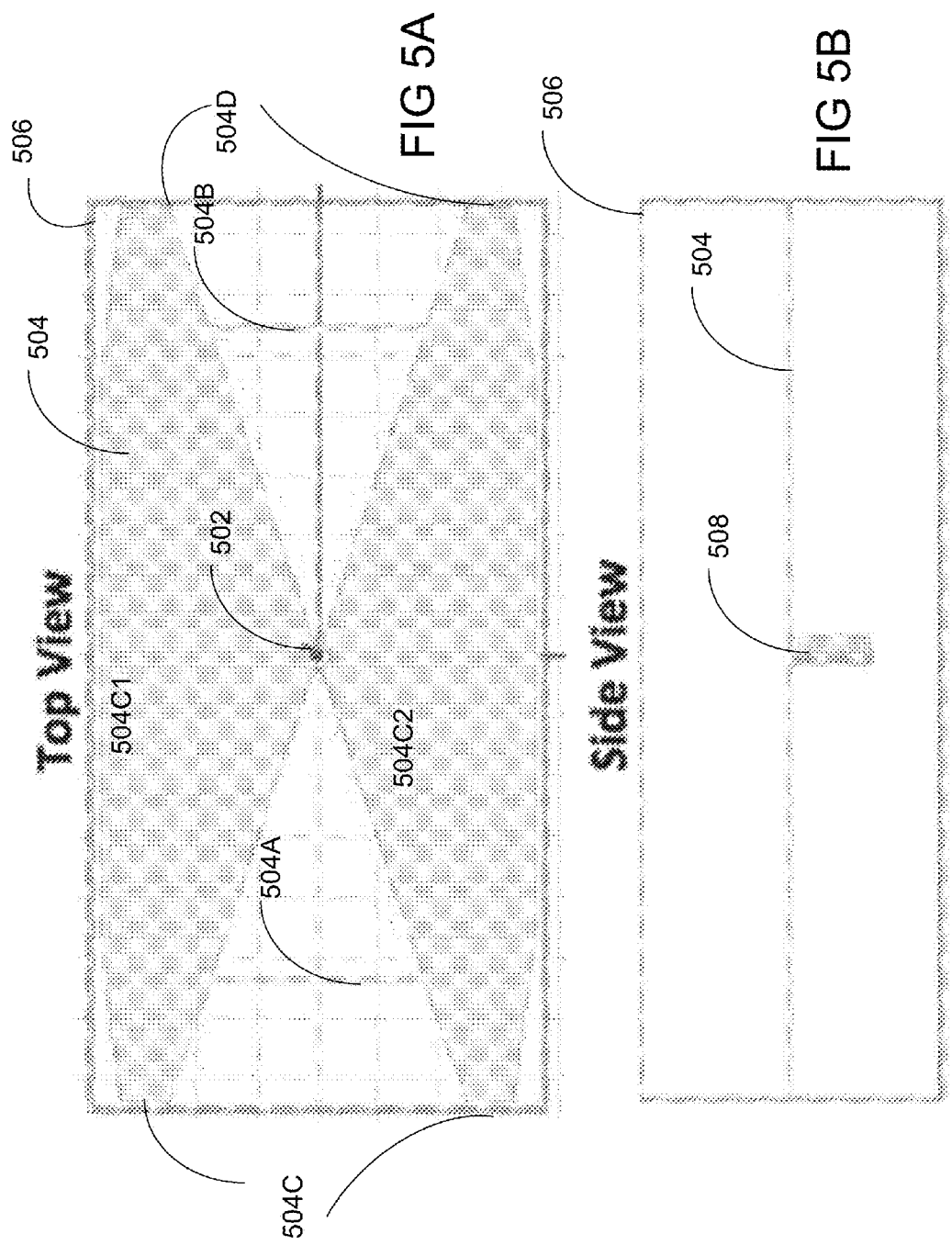

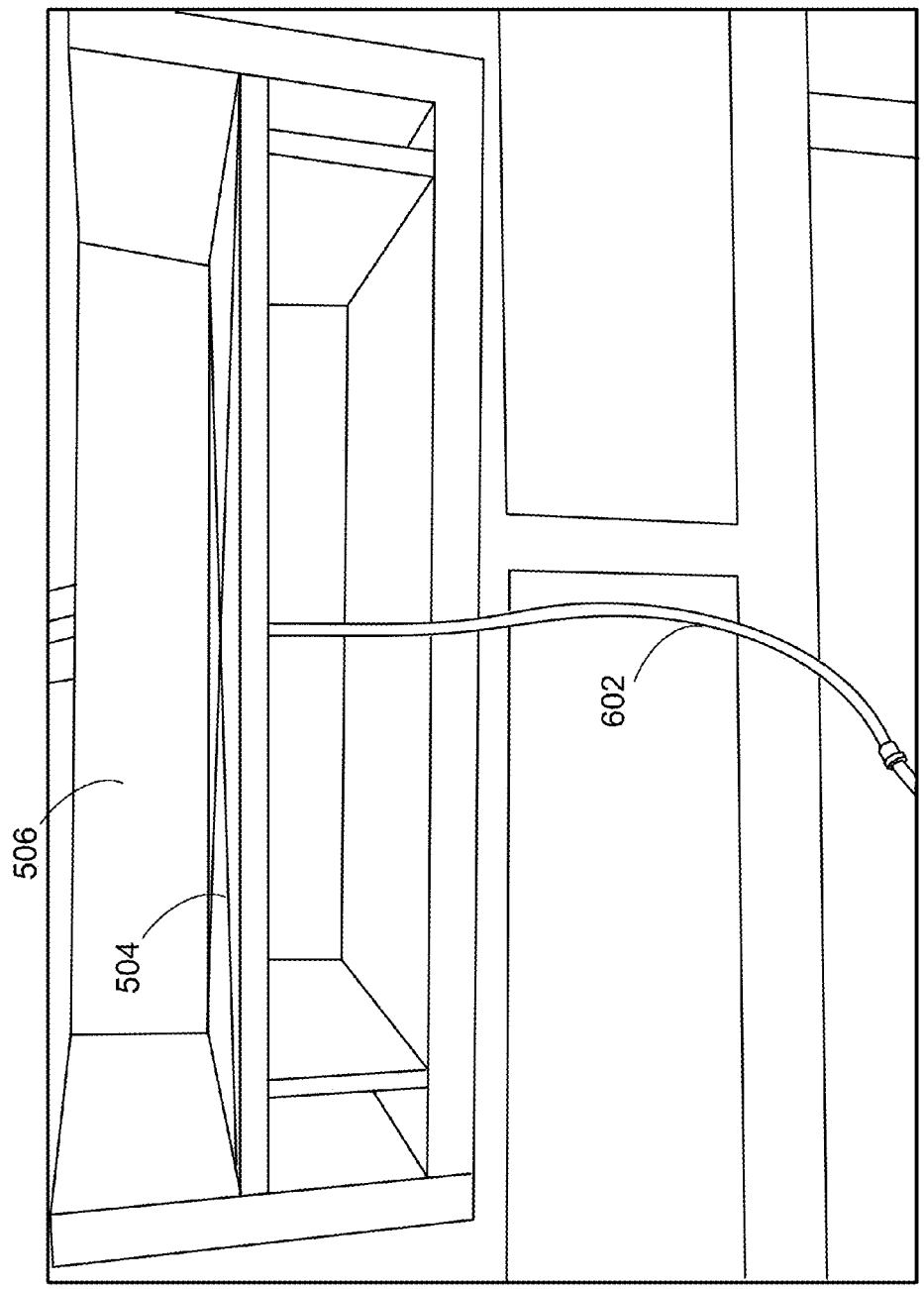

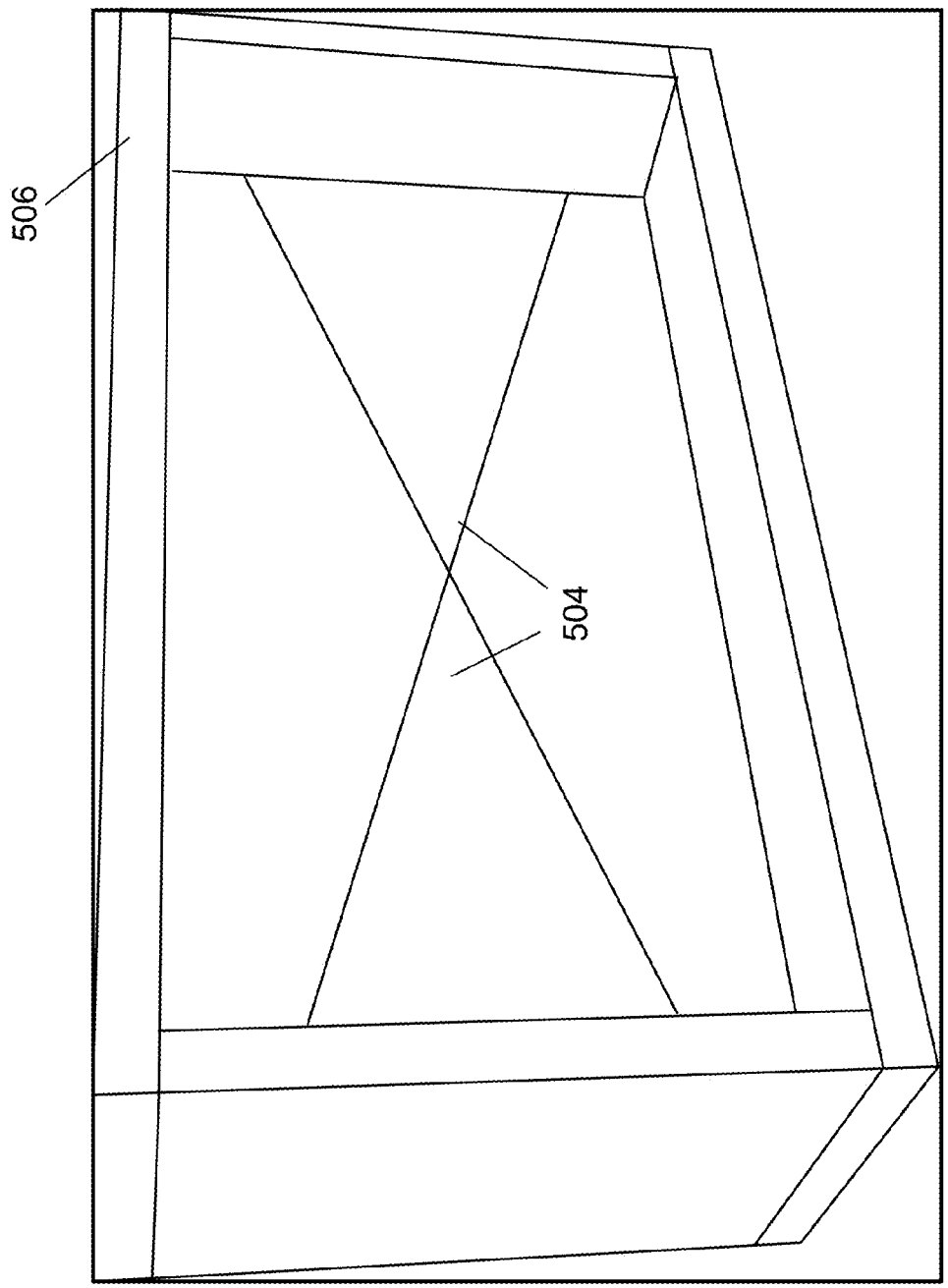

REMOTE RF POWER SYSTEM WITH LOW PROFILE TRANSMITTING ANTENNA

CROSS-REFERENCE TO RELATED APPLICATIONS

This application claims benefit from U.S. Provisional Patent Application No. 61/992,150, filed on May 12, 2014.

TECHNICAL FIELD

This application generally relates to a RF stimulation system including an antenna assembly to remotely provide power and stimulation parameters to an implantable device.

BACKGROUND

Antennas have been designed and utilized with implanted devices to aid in the treatment of various medical conditions. Often, these antennas are placed close to the patient's body. In some cases, the conductive element of the antennas would be subject to excessive absorption of electromagnetic energy, which, when these antennas are placed close to the patient's body, could lead to adverse events such as burning of tissue, creation of undesirable blood clots and skin irritation from adherence of the antenna directly to skin tissue.

SUMMARY

In one aspect, some implementations provide antenna assembly, including: an antenna that includes: a metal signal layer having a radiating surface; and a feed port; and a waveguide surrounding the antenna and configured to guide electromagnetic energy transmitted from the radiating surface in a direction away from the antenna; and a controller module connected to the feed port and configured to drive the antenna to transmit electromagnetic energy from the radiating surface; wherein the antenna, waveguide, and controller module are configured such that, when the controller module drives the antenna, the transmitted electromagnetic energy matches a reception characteristic of an implantable device and is sufficient for the implantable device to create one or more electrical pulses of sufficient amplitude to stimulate neural tissue of a patient, solely using electromagnetic energy received from the antenna, when the implantable device is located at least 10 centimeters away from the antenna.

Implementations may include one or more of the following features. The antenna assembly may further include a dielectric lens that fills the wave guide and protrude outward from an opening of the wave guide to form a protrusion that is shaped to spatially narrow the transmitted electromagnetic energy in the direction away from the transmitting surface. The protrusion may be tapered in shape. The protrusion may be tapered to have a Gaussian or sinusoid profile.

The antenna assembly may have a return loss cutoff frequency associated with the wave guide and the dielectric lens may be further configured to lower the return loss cutoff frequency. The antenna may be operable within a frequency band from about 500 MHz to about 4 GHz. The radiating surface may be bowtie shaped and has two leaf structures connecting to each other at the feed port as well as through two substantially parallel rod structures. The transmitted electromagnetic energy may be polarized along a long axis of the rod structures. The radiating surface may be adjustable from a first spatial orientation to a second spatial orientation such that polarized electromagnetic energy received at the implantable device is increased.

The waveguide may be a rectangular waveguide having four walls that surround the bowtie shaped radiating surface. The rectangular waveguide may have an interior length of about 15 cm, an interior width of about 7.6 cm, and a height of about 5 cm. The rectangular waveguide may have an interior length of at least 10 cm, and the rectangular waveguide may have an interior length, width, and height ratio of about 15:7.6:5.

In another aspect, some implementations may include a method for wirelessly supplying energy to an implantable device, the method including: radiating electromagnetic energy from a radiating surface on an antenna assembly, the radiated electromagnetic energy reaching an implantable device located at least 10 centimeters away and implanted inside a patient such that the implantable device creates, solely by using the radiated electromagnetic energy, one or more electrical stimulation pulses suitable for stimulating neural tissue of the patient, and applies the electrical stimulation pulses to neural tissue of the patient.

Implementations may include one or more of the following features. Radiating the electromagnetic energy may further include radiating the electromagnetic energy while the patient is asleep such that the created one or more electrical simulation pulses is applied to stimulate the patient's neural tissue during the patient's sleep.

The method may further include: adjusting a position of the antenna assembly such that the radiating surface of the antenna assembly is no more than six feet from the implantable device. The method may further include: adjusting a position of the antenna assembly such that the radiating surface of the antenna assembly is no less than one foot from the implantable device. The method may further include: adjusting an orientation of the antenna assembly such that the radiated electromagnetic energy received at the implantable device is increased. The method may further include: connecting the antenna assembly to a controller module; and driving the antenna assembly from the controller module connected thereto such that the radiating surface on the antenna assembly radiates electromagnetic energy to power the implantable. The method may further include establishing a link between a programming module to the controller module; and transmitting, from the programming module to the controller module, data encoding parameters of the one or more stimulation pulses to be created at the implantable device and to be subsequently applied to stimulate the patient's neural tissue.

In yet another aspect, some implementations may include a system that includes: an antenna assembly that wirelessly powers an implantable device, the antenna assembly including: an antenna that includes: a metal signal layer having a radiating surface and configured to transmit electromagnetic energy via radiative coupling; a waveguide surrounding the antenna and configured to guide electromagnetic energy transmitted from the radiating surface in a direction away from the antenna; and; a controller module connected to the feed port of the antenna and configured to drive the antenna assembly such that the radiating surface on the antenna radiates electromagnetic energy.

Implementations may include one or more of the following features. The system may further include an implantable operable from a location inside a patient and more than 10 centimeters away from the antenna assembly, wherein the implantable device creates one or more stimulation pulses of sufficient amplitude to stimulate neural tissue of the patient solely using electromagnetic energy received from the antenna assembly.

The waveguide may be a rectangular waveguide having four walls that surround the radiating surface. The rectangular waveguide may have an interior length of about 15 cm, an interior width of about 7.6 cm, and a height of about 5 cm. The rectangular waveguide may have an interior length of at least 10 cm, and the rectangular waveguide may have an interior length, width, and height ratio of about 15:7.6:5.

The system may further include a dielectric lens that fills the wave guide and protrude outward from an opening of the wave guide to form a protrusion that is shaped to spatially narrow the transmitted electromagnetic energy in the direction away from the transmitting surface. The protrusion may be tapered in shape. The protrusion may be tapered to have a Gaussian or sinusoid profile.

The antenna may be operable within a frequency band from about 500 MHz to about 4 GHz. The radiating surface may be bowtie shaped and has two leaf structures connecting to each other at the feed port as well as through two substantially parallel rod structures.

The transmitted electromagnetic energy may be polarized along a long axis of the rod structures. The implantable device may include a dipole antenna located on the implantable device inside the patient, and the radiating surface is adjustable from a first spatial orientation to a second spatial orientation such that polarized electromagnetic energy received at the dipole antenna is increased.

BRIEF DESCRIPTION OF THE DRAWINGS

FIGS. 5A-5B show an example of an antenna assembly of the wireless stimulation system.

FIGS. 6A-6C are illustrations of an antenna assembly with a wave guide.

Like reference symbols in the various drawings indicate like elements.

DETAILED DESCRIPTION

Figure 1:
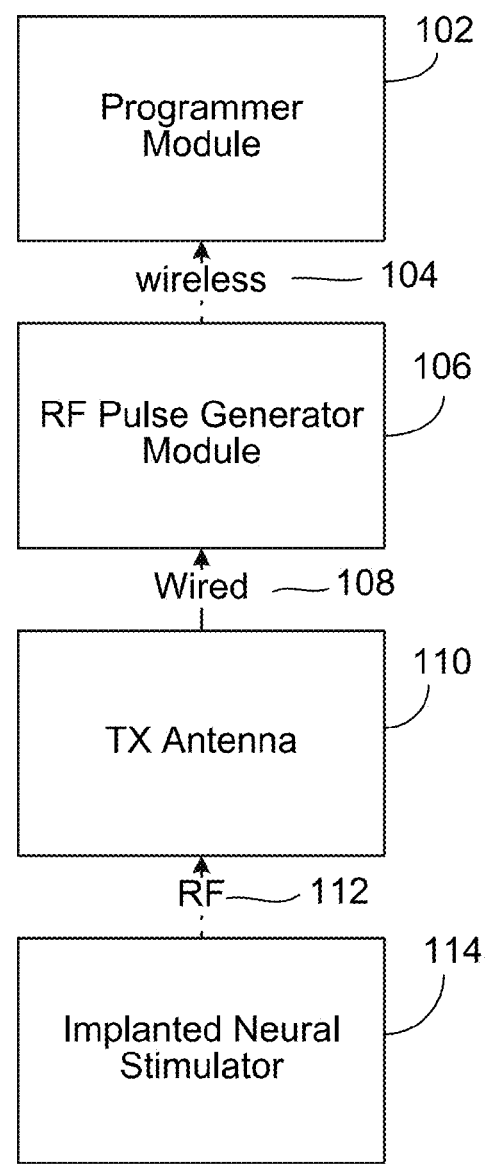
FIG. 1 depicts a high-level diagram of an example of a wireless stimulation system.

In various implementations, systems and methods are disclosed for applying one or more electrical impulses to targeted excitable tissue, such as nerves, for treating chronic pain, inflammation, arthritis, sleep apnea, seizures, incontinence, pain associated with cancer, incontinence, problems of movement initiation and control, involuntary movements, vascular insufficiency, heart arrhythmias, obesity, diabetes, craniofacial pain, such as migraines or cluster headaches, and other disorders. In certain embodiments, a device may be used to send electrical energy to targeted nerve tissue by using remote radio frequency (RF) energy without cables or inductive coupling to power a passive implanted wireless stimulator device. The targeted nerves can include, but are not limited to, the spinal cord and surrounding areas, including the dorsal horn, dorsal root ganglion, the exiting nerve roots, nerve ganglions, the dorsal column fibers and the peripheral nerve bundles leaving the dorsal column and brain, such as the vagus, occipital, trigeminal, hypoglossal, sacral, coccygeal nerves and the like.

A wireless stimulation system can include an implantable stimulator device with one or more electrodes and one or more conductive antennas (for example, dipole or patch antennas), and internal circuitry for frequency waveform and electrical energy rectification. The system may further comprise an external controller and antenna for transmitting radio frequency or microwave energy from an external source to the implantable stimulator device with neither cables nor inductive coupling to provide power.

In various implementations, the wireless implantable stimulator device is powered wirelessly (and therefore does not require a wired connection) and contains the circuitry necessary to receive the pulse instructions from a source external to the body. For example, various embodiments employ internal dipole (or other) antenna configuration(s) to receive RF power through electrical radiative coupling. This allows such devices to produce electrical currents capable of stimulating nerve bundles without a physical connection to an implantable pulse generator (IPG) or use of an inductive coil.

Antennas can be designed for the purpose of transmitting microwave energy to a receiving antenna located just below a patient's skin, or on the skin, from a distant location (e.g., of up to four to six feet and stationary). The antenna design may be dependent on the mobility needs of the patient while receiving the therapy. The antenna may advantageously have a minimum profile so that the antenna can blend in with the ambiance of the room. The disclosure focuses on the design of a compact remote transmitting antenna with superior matching and gain, as well as being several orders of magnitude less expensive than comparable antennas and very easy to manufacture.

According to some implementations, a wireless stimulation system can include an antenna assembly coupled to a controller module and configured to radiate electromagnetic energy to an implantable device. In some instances, the implantable device can be a passive neural stimulator device configured to receive RF energy and stimulation parameters wirelessly. Solely by using the received electromagnetic energy, the implantable passive neural stimulator creates one or more stimulation pulses to stimulate neural tissue of a patient. In particular, the antenna assembly can include an antenna with a bowtie-shaped radiating surface and a feed port. The feed port may be coupled to a controller module that drives the antenna to transmit the electromagnetic energy from the bowtie radiating surface. The bowtie shaped radiating surface is generally sized and shaped to radiate the electromagnetic energy to match a reception characteristic of the implantable passive neural stimulator. In one example, the implantable passive neural stimulator includes a dipole antenna and the radiating surface is configured to transmit polarized electromagnetic energy commensurate with dipole reception characteristics. Moreover, the antenna assembly may further include a wave guide that surrounds the antenna to direct the transmitted electromagnetic energy away from the radiating surface. In some instances, a dielectric lens fills the waveguide and extend outward from an opening of the wave guide to form a protrusion. The protrusion is shaped to spatially narrow the transmitted electromagnetic energy in the direction away from the transmitting surface. The protrusion may be tapered in shape and may have a Gaussian or sinusoid profile.

Further descriptions of exemplary wireless systems for providing neural stimulation to a patient can be found in commonly-assigned, co-pending published PCT applications PCT/US2012/23029 filed Jan. 28, 2011, PCT/US2012/32200 filed Apr. 11, 2011, PCT/US2012/48903, filed Jan. 28, 2011, PCT/US2012/50633, filed Aug. 12, 2011 and PCT/US2012/55746, filed Sep. 15, 2011, the complete disclosures of which are incorporated by reference.

FIG. 1 depicts a high-level diagram of an example of a wireless stimulation system. The wireless stimulation system may include four major components, namely, a programmer module 102, a RF pulse generator module 106, a transmit (TX) antenna 110 (for example, a patch antenna, slot antenna, or a dipole antenna), and an implanted wireless stimulator device 114. The programmer module 102 may be a computer device, such as a smart phone, running a software application that supports a wireless connection 104, such as Bluetooth®. The application can enable the user to view the system status and diagnostics, change various parameters, increase/decrease the desired stimulus amplitude of the electrode pulses, and adjust feedback sensitivity of the RF pulse generator module 106, among other functions.

The RF pulse generator module 106 may include communication electronics that support the wireless connection 104, the stimulation circuitry, and the battery to power the generator electronics. In some implementations, the RF pulse generator module 106 includes the TX antenna embedded into its packaging form factor while, in other implementations, the TX antenna is connected to the RF pulse generator module 106 through a wired connection 108 or a wireless connection (not shown). The TX antenna 110 may be coupled directly to tissue to create an electric field that powers the implanted wireless stimulator device 114. The TX antenna 110 communicates with the implanted wireless stimulator device 114 through an RF interface. For instance, the TX antenna 110 radiates an RF transmission signal that is modulated and encoded by the RF pulse generator module 110. The implanted wireless stimulator device of module 114 contains one or more antennas, such as dipole antenna(s), to receive and transmit through RF interface 112. In particular, the coupling mechanism between antenna 110 and the one or more antennas on the implanted wireless stimulation device of module 114 utilizes electrical radiative coupling and not inductive coupling. In other words, the coupling is through an electric field rather than a magnetic field.

Through this electrical radiative coupling, the TX antenna 110 can provide an input signal to the implanted wireless stimulator device 114. This input signal contains energy and may contain information encoding stimulus waveforms to be applied at the electrodes of the implanted wireless stimulator device 114. In some implementations, the power level of this input signal directly determines an applied amplitude (for example, power, current, or voltage) of the one or more electrical pulses created using the electrical energy contained in the input signal. Within the implanted wireless stimulator device 114 are components for demodulating the RF transmission signal, and electrodes to deliver the stimulation to surrounding neuronal tissue.

The RF pulse generator module 106 can be implanted subcutaneously, or it can be worn external to the body. When external to the body, the RF generator module 106 can be incorporated into a belt or harness design to allow for electric radiative coupling through the skin and underlying tissue to transfer power and/or control parameters to the implanted wireless stimulator device 114. In either event, receiver circuit(s) internal to the wireless stimulator device 114 (or cylindrical wireless implantable stimulator device 1400 shown in FIGS. 14A and 14B, helical wireless implantable stimulator device 1900 shown in FIGS. 19A to 19C) can capture the energy radiated by the TX antenna 110 and convert this energy to an electrical waveform. The receiver circuit(s) may further modify the waveform to create an electrical pulse suitable for the stimulation of neural tissue.

In some implementations, the RF pulse generator module 106 can remotely control the stimulus parameters (that is, the parameters of the electrical pulses applied to the neural tissue) and monitor feedback from the wireless stimulator device 114 based on RF signals received from the implanted wireless stimulator device 114. A feedback detection algorithm implemented by the RF pulse generator module 106 can monitor data sent wirelessly from the implanted wireless stimulator device 114, including information about the energy that the implanted wireless stimulator device 114 is receiving from the RF pulse generator and information about the stimulus waveform being delivered to the electrode pads. In order to provide an effective therapy for a given medical condition, the system can be tuned to provide the optimal amount of excitation or inhibition to the nerve fibers by electrical stimulation. A closed loop feedback control method can be used in which the output signals from the implanted wireless stimulator device 114 are monitored and used to determine the appropriate level of neural stimulation current for maintaining effective neuronal activation, or, in some cases, the patient can manually adjust the output signals in an open loop control method.

Figure 2:
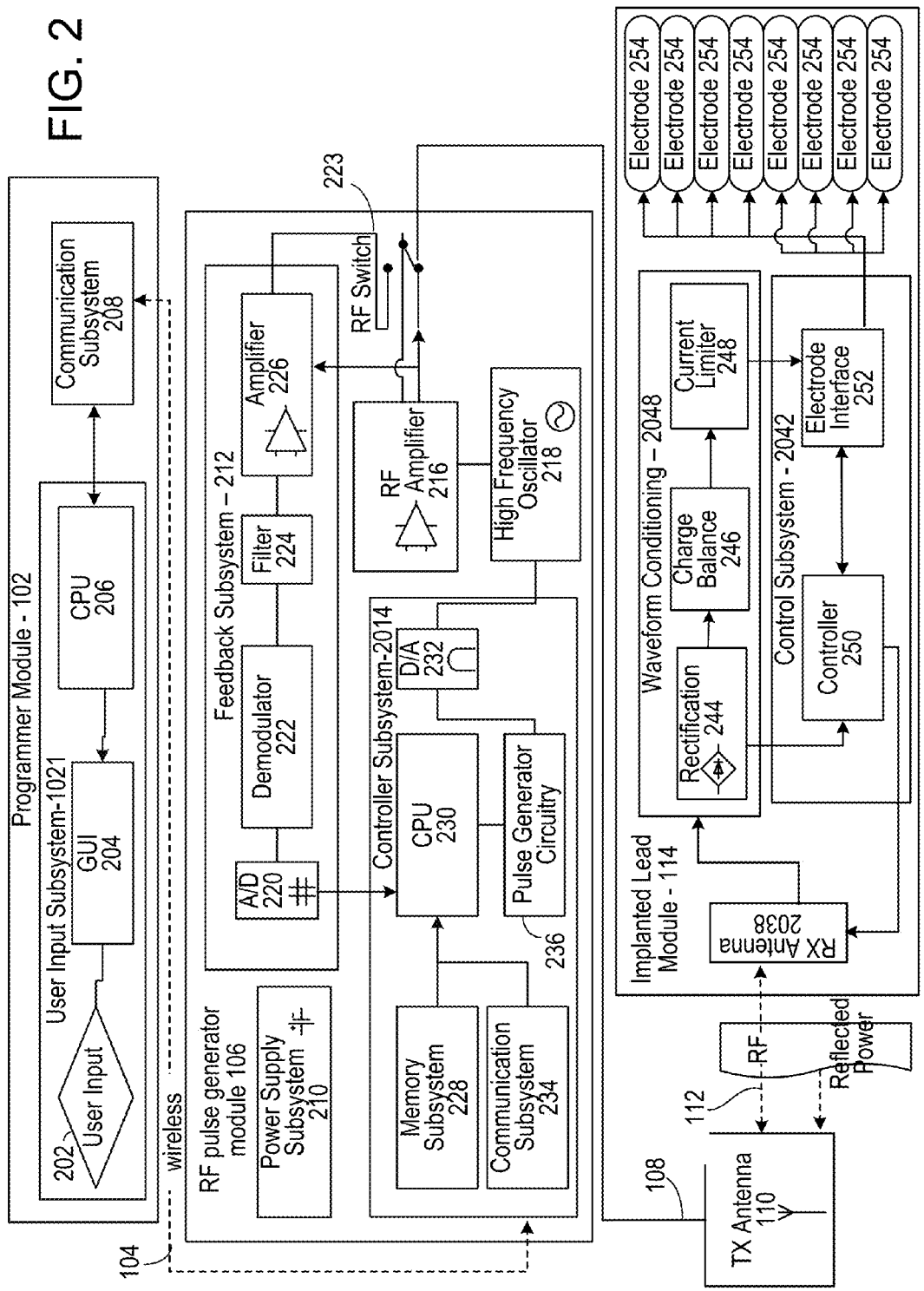
FIG. 2 depicts a detailed diagram of an example of the wireless stimulation system.

FIG. 2 depicts a detailed diagram of an example of the wireless stimulation system. As depicted, the programming module 102 may comprise user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 104, such as Bluetooth or Wi-Fi, to the RF pulse generator module 106, as well as receive data from module 106.

For instance, the programmer module 102, which can be utilized for multiple users, such as a patient's control unit or clinician's programmer unit, can be used to send stimulation parameters to the RF pulse generator module 106. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

TABLE 1

| Stimulation Parameter | |
| --- | --- |
| Pulse Amplitude: | 0 to 20 mA |
| Pulse Frequency: | 0 to 10000 Hz |
| Pulse Width: | 0 to 2 ms |

The RF pulse generator module 106 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 102 may be functionally a smart device and associated application. The smart device hardware may include a CPU 206 and be used as a vehicle to handle touchscreen input on a graphical user interface (GUI) 204, for processing and storing data.

The RF pulse generator module 106 may be connected via wired connection 108 to an external TX antenna 110. Alternatively, both the antenna and the RF pulse generator are located subcutaneously (not shown).

The signals sent by RF pulse generator module 106 to the implanted wireless stimulator device 114 may include both power and parameter-setting attributes in regards to stimulus waveform, amplitude, pulse width, and frequency. The RF pulse generator module 106 can also function as a wireless receiving unit that receives feedback signals from the implanted wireless stimulator device 114. To that end, the RF pulse generator module 106 may contain microelectronics or other circuitry to handle the generation of the signals transmitted to the device 114 as well as handle feedback signals, such as those from the stimulator device 114. For example, the RF pulse generator module 106 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 102 (including receiving stimulation parameters from programmer module), pulse generator circuitry 236, and digital/analog (D/A) converters 232.

The controller subsystem 214 may be used by the patient and/or the clinician to control the stimulation parameter settings (for example, by controlling the parameters of the signal sent from RF pulse generator module 106 to the stimulator device 114). These parameter settings can affect, for example, the power, current level, or shape of the one or more electrical pulses. The programming of the stimulation parameters can be performed using the programming module 102, as described above, to set the repetition rate, pulse width, amplitude, and waveform that will be transmitted by RF energy to the receiving (RX) antenna 238, typically a dipole antenna (although other types may be used), in the implanted wireless stimulation device 214. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 214 may store received parameter settings in the local memory subsystem 228, until the parameter settings are modified by new input data received from the programming module 102. The CPU 206 may use the parameters stored in the local memory to control the pulse generator circuitry 236 to generate a stimulus waveform that is modulated by a high frequency oscillator 218 in the range from 300 MHz to 8 GHz (preferably between about 700 MHz and 5.8 GHz and more preferably between about 800 MHz and 1.3 GHz). The resulting RF signal may then be amplified by RF amplifier 226 and then sent through an RF switch 223 to the TX antenna 110 to reach through depths of tissue to the RX antenna 238.

In some implementations, the RF signal sent by TX antenna 110 may simply be a power transmission signal used by the wireless stimulation device module 114 to generate electric pulses. In other implementations, a telemetry signal may also be transmitted to the wireless stimulator device 114 to send instructions about the various operations of the wireless stimulator device 114. The telemetry signal may be sent by the modulation of the carrier signal (through the skin if external, or through other body tissues if the pulse generator module 106 is implanted subcutaneously). The telemetry signal is used to modulate the carrier signal (a high frequency signal) that is coupled onto the implanted antenna(s) 238 and does not interfere with the input received on the same stimulator device to power the device. In one embodiment the telemetry signal and powering signal are combined into one signal, where the RF telemetry signal is used to modulate the RF powering signal, and thus the wireless stimulation device is powered directly by the received telemetry signal; separate subsystems in the wireless stimulation device harness the power contained in the signal and interpret the data content of the signal.

The RF switch 223 may be a multipurpose device such as a dual directional coupler, which passes the relatively high amplitude, extremely short duration RF pulse to the TX antenna 110 with minimal insertion loss while simultaneously providing two low-level outputs to feedback subsystem 212; one output delivers a forward power signal to the feedback subsystem 212, where the forward power signal is an attenuated version of the RF pulse sent to the TX antenna 110, and the other output delivers a reverse power signal to a different port of the feedback subsystem 212, where reverse power is an attenuated version of the reflected RF energy from the TX Antenna 110.

During the on-cycle time (when an RF signal is being transmitted to wireless stimulator device 114), the RF switch 223 is set to send the forward power signal to feedback subsystem. During the off-cycle time (when an RF signal is not being transmitted to the wireless stimulator device 114), the RF switch 223 can change to a receiving mode in which the reflected RF energy and/or RF signals from the wireless stimulator device 114 are received to be analyzed in the feedback subsystem 212.

The feedback subsystem 212 of the RF pulse generator module 106 may include reception circuitry to receive and extract telemetry or other feedback signals from the wireless stimulator device 114 and/or reflected RF energy from the signal sent by TX antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 106. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 110 has perfectly matched impedance to the tissue that it contacts, the electromagnetic waves generated from the RF pulse generator 106 pass unimpeded from the TX antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the TX antenna 110 with the body surface. When such a mismatch occurs, the electromagnetic waves sent from the RF pulse generator 106 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 106. For example, for a moderate degree of reflected power the course of action can be for the controller subsystem 214 to increase the amplitude of RF power sent to the TX antenna 110, as would be needed to compensate for slightly non-optimum but acceptable TX antenna coupling to the body. For higher ratios of reflected power, the course of action can be to prevent operation of the RF pulse generator 106 and set a fault code to indicate that the TX antenna 110 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can lead to unwanted heating of internal components, and this fault condition means the system cannot deliver sufficient power to the implanted wireless stimulation device and thus cannot deliver therapy to the user.

The controller 242 of the wireless stimulator device 114 may transmit informational signals, such as a telemetry signal, through the antenna 238 to communicate with the RF pulse generator module 106 during its receive cycle. For example, the telemetry signal from the wireless stimulator device 114 may be coupled to the modulated signal on the dipole antenna(s) 238, during the on and off state of the transistor circuit to enable or disable a waveform that produces the corresponding RF bursts necessary to transmit to the external (or remotely implanted) pulse generator module 106. The antenna(s) 238 may be connected to electrodes 254 in contact with tissue to provide a return path for the transmitted signal. An A/D (not shown) converter can be used to transfer stored data to a serialized pattern that can be transmitted on the pulse-modulated signal from the internal antenna(s) 238 of the wireless stimulator device 114.

A telemetry signal from the implanted wireless stimulator device 114 may include stimulus parameters such as the power or the amplitude of the current that is delivered to the tissue from the electrodes. The feedback signal can be transmitted to the RF pulse generator module 116 to indicate the strength of the stimulus at the nerve bundle by means of coupling the signal to the implanted RX antenna 238, which radiates the telemetry signal to the external (or remotely implanted) RF pulse generator module 106. The feedback signal can include either or both an analog and digital telemetry pulse modulated carrier signal. Data such as stimulation pulse parameters and measured characteristics of stimulator performance can be stored in an internal memory device within the implanted stimulator device 114, and sent on the telemetry signal. The frequency of the carrier signal may be in the range of at 300 MHz to 8 GHz (preferably between about 700 MHz and 5.8 GHz and more preferably between about 800 MHz and 1.3 GHz).

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify the wireless stimulator device 114 delivered the specified stimuli to tissue. For example, if the wireless stimulation device reports a lower current than was specified, the power level from the RF pulse generator module 106 can be increased so that the implanted wireless stimulator device 114 will have more available power for stimulation. The implanted wireless stimulator device 114 can generate telemetry data in real time, for example, at a rate of 8 Kbits per second. All feedback data received from the implanted stimulator device 114 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the implantable wireless stimulator device 114 by the control subsystem 242 and routed to the appropriate electrodes 254 that are placed in proximity to the tissue to be stimulated. For instance, the RF signal transmitted from the RF pulse generator module 106 may be received by RX antenna 238 and processed by circuitry, such as waveform conditioning circuitry 240, within the implanted wireless stimulator device 114 to be converted into electrical pulses applied to the electrodes 254 through electrode interface 252. In some implementations, the implanted wireless stimulator device 114 contains between two to sixteen electrodes 254.

The waveform conditioning circuitry 240 may include a rectifier 244, which rectifies the signal received by the RX antenna 238. The rectified signal may be fed to the controller 242 for receiving encoded instructions from the RF pulse generator module 106. The rectifier signal may also be fed to a charge balance component 246 that is configured to create one or more electrical pulses based such that the one or more electrical pulses result in a substantially zero net charge at the one or more electrodes (that is, the pulses are charge balanced). The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless stimulator device 114 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the pulse generator 106. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the pulse generator 106 can reduce the RF power delivered to the body if the implanted wireless stimulator device 114 reports it is receiving excess RF power.

The controller 250 of the stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 106 has multiple electrodes 254 in contact with tissue, and for a given stimulus the RF pulse generator module 106 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

Also, in some implementations, for a given stimulus pulse, the controller 250 may control the electrode interface 252 to divide the current arbitrarily (or according to instructions from pulse generator module 106) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 250, on its own or in response to instructions from pulse generator 106, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 250 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 250 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 250 was configured to match the repetition rate for set B to that of set A, for such a case the controller 250 can specify the relative start times of the stimulus cycles to be coincident in time or to be arbitrarily offset from one another by some delay interval.

In some implementations, the controller 250 can arbitrarily shape the stimulus waveform amplitude, and may do so in response to instructions from pulse generator 106. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the wireless stimulator device 114 may include a charge-balancing component 246. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units $uC/cm^2$. In order to avoid the irreversible electrochemical reactions such as pH change, electrode dissolution as well as tissue destruction, no net charge should appear at the electrode-electrolyte interface, and it is generally acceptable to have a charge density less than 30 uC/cm$^2$. Biphasic stimulating current pulses ensure that no net charge appears at the electrode after each stimulation cycle and the electrochemical processes are balanced to prevent net dc currents. The wireless stimulator device 114 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 246 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment as disclosed herein, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless stimulator device 114 may create a drive-waveform envelope that follows the envelope of the RF pulse received by the receiving dipole antenna(s) 238. In this case, the RF pulse generator module 106 can directly control the envelope of the drive waveform within the wireless stimulator device 114, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted wireless stimulator device 114 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 106, and in others this control may be administered internally by circuitry onboard the wireless stimulator device 114, such as controller 250. In the case of onboard control, the amplitude and timing may be specified or modified by data commands delivered from the pulse generator module 106.

In some applications, the transmit antenna 110 can be placed in close proximity to the receiving antenna 238. For example, the transmit antenna 110 may be worn by the patient. In other examples, the transmit antenna 110 may be placed further away from the patient (and the implanted passive neural stimulator that houses receiving antenna 238). In the former case, less energy may be emitted from the remote antenna to wirelessly provide power and stimulation parameter settings to the passive neural stimulator. In some scenarios, the patient may remain stationary or asleep. During sleep, the patient may not desire to wear a transmitting antenna 110 that is coupled to a controller module (such as controller subsystem 214) through a cable. An antenna assembly may be used to remotely provide power and stimulation parameter settings to the passive neural stimulator. The antenna assembly in this example may be more than 10 centimeters away from the passive neural stimulator implanted inside a patient. If the patient can move around a room; the entire room may need to be illuminated with the microwave energy field. In this scenario, an array of antennas, or a broad beam-width antenna, may be used. Some implementations may incorporate a steerable (e.g., mechanically, electrically) arrangement of antennas that include a receiving antenna location tracking system. These implementations may further apply motion control of the transmitting antenna 110 to adjust angle or orientation of illumination of an antenna to point in the direction of the receiving antenna. The output power is adjusted as needed depending on the distance between the transmitting and receiving antennas and the directivity of the transmitting antenna.

Figure 3A:
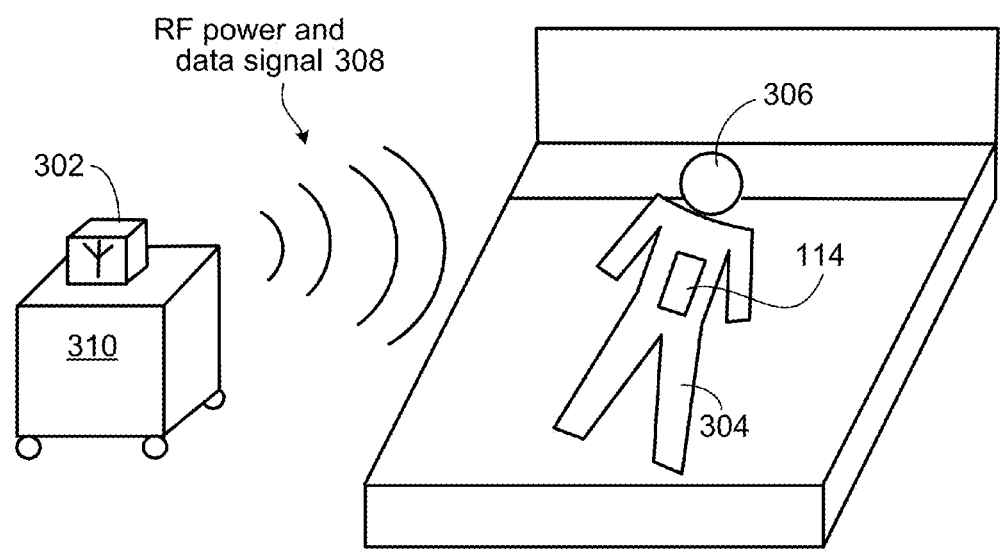
FIGS. 3A-3C show examples of operations of a microwave stimulation system.
Figure 3B:
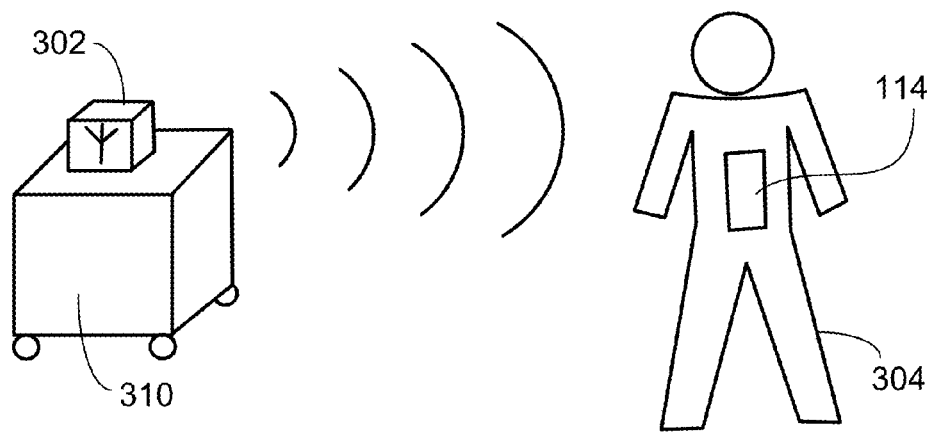
Figure 3C:
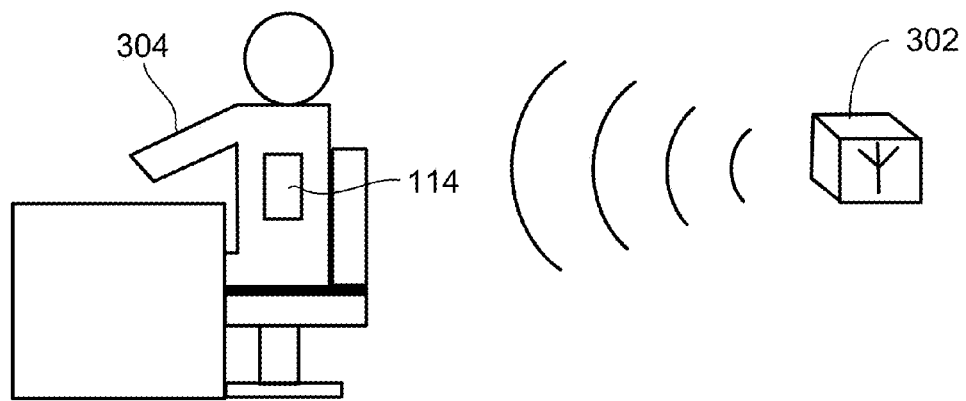

FIGS. 3A-3C show examples of operations of a RF stimulation system. These examples may incorporate a single remote transmitting antenna or an array of transmitting antennas. In some instances, the array may be steerable to focus on a particular location. In other instances, the transmitting antenna(s) may be fixed.

In FIG. 3A, a patient 304 implanted with a neural stimulator device 114 is resting in bed 306 while receiving therapy from a transmitting antenna system 302 (e.g., transmitting antenna 110 and controller subsystem 214). As illustrated, the transmitting antenna system 302 is placed elsewhere in the same room to transmit electromagnetic energy 308 including power and stimulation parameters to implanted neural stimulator device 114. For example, the remote transmitting antenna system 302 may be placed on a dresser 310 or a night-stand near the patient bed. The remote transmitting antenna 310 system may be battery or wall powered. The remote transmitting antenna system 310 may receive programming or therapeutic instructions manually via physical buttons (or other tactile user interface on controller subsystem 214) or by a wireless instruction protocol such as Bluetooth or RF (e.g., cellular, Wi-Fi, etc.) from a programming module (not shown). The patient 304 may control the remote transmitting antenna system 302 via the physical buttons or Bluetooth.

FIG. 3B depicts a similar scenario of transmitting electromagnetic energy 308 to remotely provide power and stimulator parameters to an implanted neural stimulator device 114 while patient 304 is standing or walking around without a wearable antenna system. In this illustration, transmitting antenna system 302 (e.g., transmitting antenna 110 and controller subsystem 214) is placed on arbitrary furniture 320 in the same room as the standing or walking patient.

FIG. 3C depicts another similar scenario in which patient 304 with implanted neural stimulator device 114 is sitting away from transmitting antenna system 302 (e.g., transmitting antenna 110 and controller subsystem 214). For example, patient 304 may sit in an office chair. In this illustration, electromagnetic energy 308 is transmitted from transmitting antenna system 302 to remotely provide power and stimulation parameters to an implanted neural stimulator device 114.

Figure 4A:
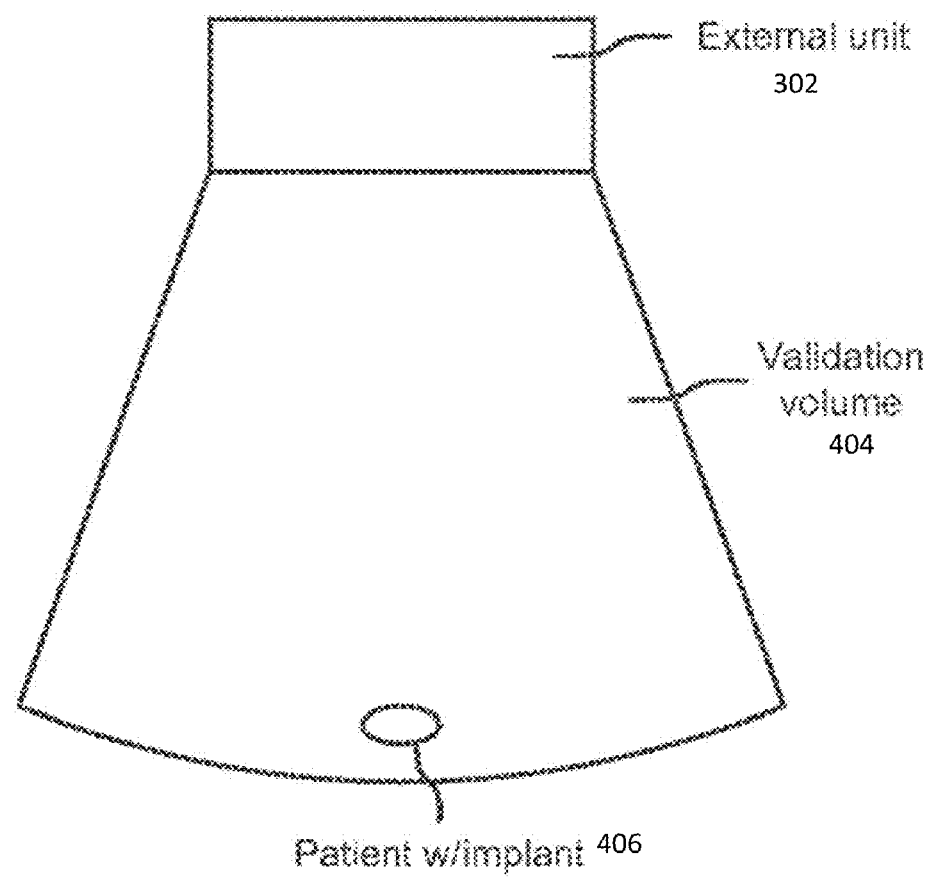
FIGS. 4A-4B show examples of radiation volumes when the microwave stimulation system is in operation.

FIG. 4A illustrates a top view of radiation volume 404 as transmitted from the remote transmitting antenna system 302. More particularly, the range of the remote transmitting antenna system 302 is shown as generally conical and directional, extending in one direction from the remote transmitting antenna system 302. Generally, the patient 406 may need to stay within the radiation volume to receive the desired stimulation therapy. The volume may interact with a standing or sitting patient (i.e., the remote transmitting antenna system may be configured to interact with an implanted antenna within a given distance and effective angle from the remote antenna).

Figure 4B:
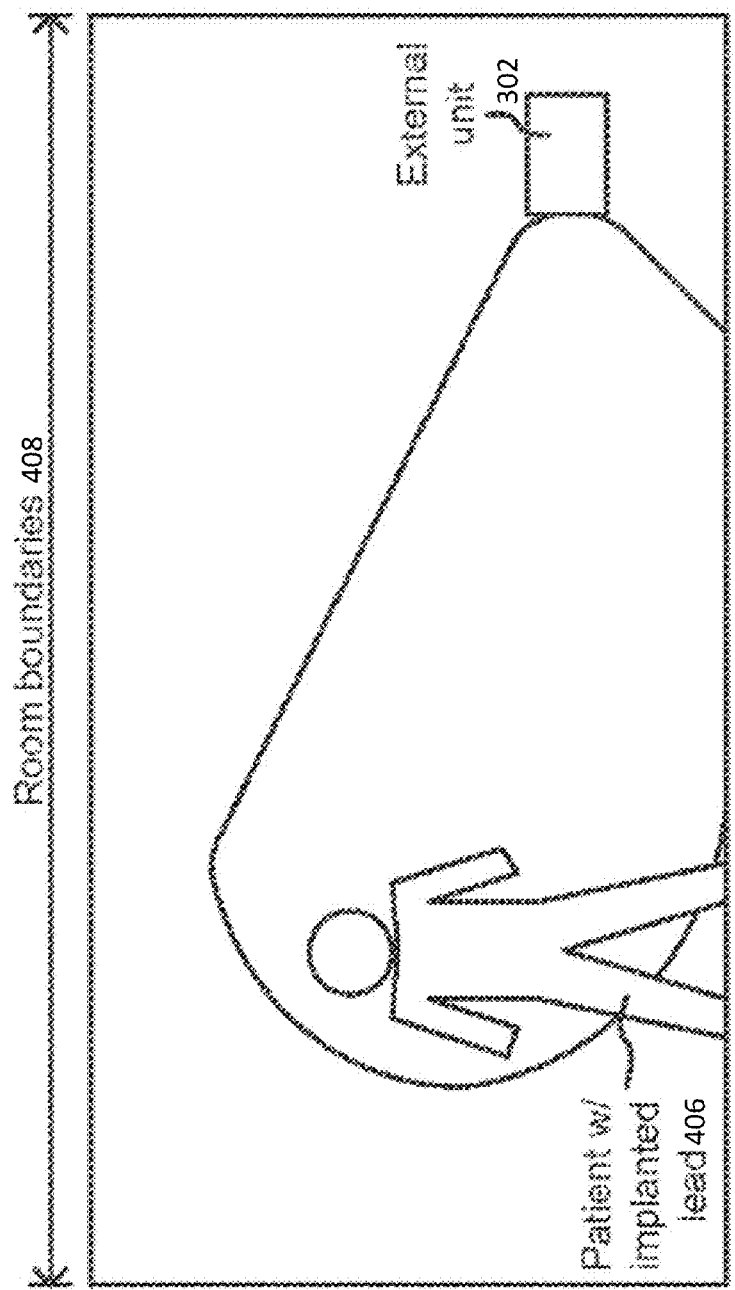

FIG. 4B illustrates a side and three-dimensional view of radiation volume 404 as generated by the remote transmitting antenna system 302. In this illustration, the system radiation volume 404 can cover a patient 406 standing within the effective angles/distances to generate an effective electric field at the receiving antenna on implanted neural stimulator device 114 while the patient is standing.

In these illustrations, wireless transmission of power and stimulation parameters generally operate by line of sight. In other words, transmitting antenna system 302 generally emits electromagnetic radiation through free space and then into the human body and implanted neural stimulator device 114. Blocking objects, such as those with lossy conducting material (e.g., low permittivity) or a material that reflects RF, such as metals, may negatively impact wireless transmission.

In these illustrations, the position of transmitting antenna system 302 may be adjusted such that a radiating surface of transmitting antenna system 302 is no less than one foot from the implanted neural stimulator device. In this configuration, transmitting antenna system 302 may not be a wearable gear for the patient. The position of transmitting antenna system 302 may also be adjusted such that the radiating surface of transmitting antenna system 302 is no more than six foot from the implanted neural stimulator device in order for the implantable neural stimulator device to receive sufficient operating energy wirelessly from the transmitting antenna system 302. Transmitting antenna system 302 may radiate polarized electromagnetic energy and an orientation of a transmitting antenna on the transmitting antenna system 302 may be adjusted so that the transmitting antenna is better aligned with the receiving antenna on the implantable neural stimulator device. When the alignment is improved through re-orientation, electromagnetic energy received at the receiving antenna can be increased as well.

Referring generally to FIGS. 5A-5B, the general design of the UWB antenna (i.e., for the remote transmitting antenna system 302) is shown. As illustrated, remote transmitting antenna system 302 includes a rectangular aperture waveguide 506 surrounding the antenna having a radiating surface 504 and a feed port 502. Feed port 502 may include a cable connector 508 for coupling to a cable. Example connectors may include BNC (Bayonet Neill-Concelman) connector, or SMA (SubMiniature version A) connectors.

In this example, the radiating surface 504 of the antenna is bowtie-shaped. In addition to two leaf structures 504C1 and 504C2, this bowtie shape also includes two rod structures 504A and 504B connecting the two leaf structures. The bowtie-shaped radiating surface 504 has contacts 504C and 504D connecting wave guide 506. The bowtie antenna distributes electromagnetic field in wave guide 506 and induces wave guide mode of propagation polarized along, for example, a long axis of rod structures 504A and 504B. The bowtie antenna may radiate over a wide bandwidth like a dipole. Surrounding the antenna with waveguide 506 improves directivity of the antenna. Scaling the antenna size can determine the bandwidth of the antenna. In one implementation, the antenna size may be scaled such that the antenna is parameterized to have a band from 500 MHz to 4 GHz. The scaling may be simplified to just the length, width, and height of the interior of the rectangular waveguide.

One example of optimized dimensions of the antenna are presented in Table 1 below:

TABLE 1

| UWB Antenna example dimensions following parameterization | |
|---|---|
| Optimized UWB Antenna Dimension | Value [units] |
| Length of the Waveguide (Interior) | 30 [cm] |
| Width of the Waveguide (Interior) | 15 [cm] |
| Height of the Waveguide (Interior) | 10.03 [cm] |

The waveguide dimensions may be scaled with the operating frequency of the bowtie-shaped antenna. For context, each wave guide has a cut-off frequency beyond which the wave guide cannot support wave propagation. When a wave guide surrounds a transmitting antenna, for example the bowtie shaped antenna as illustrated, the wave guide needs to be large enough to support the propagation of the electromagnetic wave from the transmitting antenna. Yet, it is advantageous to have a compact transmitting antenna system for applications as depicted in FIGS. 3A-3C.

The bowtie antenna assembly as depicted herein may be smaller in size than horn antennas operating at the same frequency. In some instances, bowtie antenna assembly can be a factor of 2 to 3 smaller than a horn antenna operating at the same frequency. In addition to a reduction of the waveguide cross-section and total length, the directivity of the bowtie antenna assembly may also be controlled. In some instances, the antenna may include a tapered dielectric transition from the mouth of the waveguide and over the radiating surface. The tapering may match the waveguide at the mouth so that the reflection back to the feed port 508 is reduced. The tapering may also focus the main beam of the bowtie antenna by spatially narrowing the beam width. For example, tapering in one spatial dimension can lead to narrowing of the beam width of the transmitted electromagnetic beam in the same dimension.

The design for an ultra-wide band (UWB) antenna is shown below, with analysis through modeling. Strong correlation is demonstrated between the theoretical results and the actual measured results from a prototype, thereby verifying the accuracy and validity of the simulation model. Generally, cavity backed rectangular aperture antennas (CB-RAA, as used herein) have performance characteristics that lend themselves well to the remote antenna application. CB-RAA can possess radiation characteristics for radiating over a wide bandwidth. Further, its radiation efficiency is very close to that from a circular aperture (81% vs. 83.6%), while the electric field lines of CB-RAA are parallel, thereby improving the cross-polarization performance when the transmission is off the bore sight of the transmitting antenna 110.

These features for the UWB antenna may be incorporated into the transmitting antenna 110 discussed herein. The remote transmitting antenna 110 is advantageously a directional, efficient, and far reaching antenna, all while relatively simple and easy to manufacture. The cross-polarization and E-field orientation for the transmitting antenna 110 may allow for a range of positions for placing the antenna such that sufficient energy reaches the implanted antenna to power the same. The large bandwidth response associated with addition of the waveguide and focusing lens may allow fine-tuning of the transmitting antenna 110 to a particular frequency, thereby rendering antenna more capable to operate at various particular frequencies.

Figure 6A:
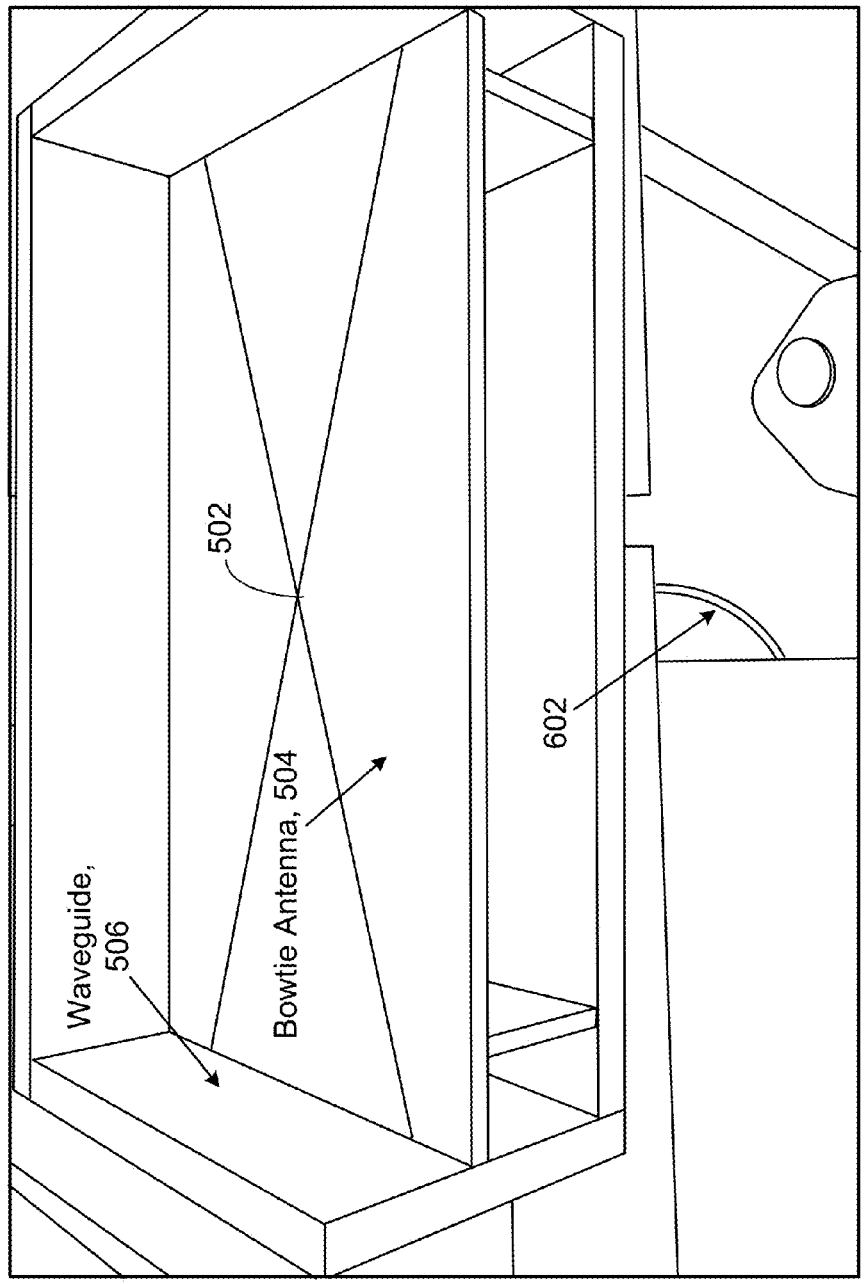

Referring to FIGS. 6A-6C, an example of an antenna assembly with a wave guide are shown. In FIGS. 6A-6B, a side plate is removed to reveal the internal structure of the antenna assembly, which includes the transmitting antenna 110 with a bowtie-shaped radiating surface and a feed port coupled to a cable connector. FIG. 6C depicts an intact antenna assembly (with no sidewalls removed). The dimensions match the dimensions of the target antenna model (shown in Table 1) within a tolerance of ±0.5 mm.

Figure 7:
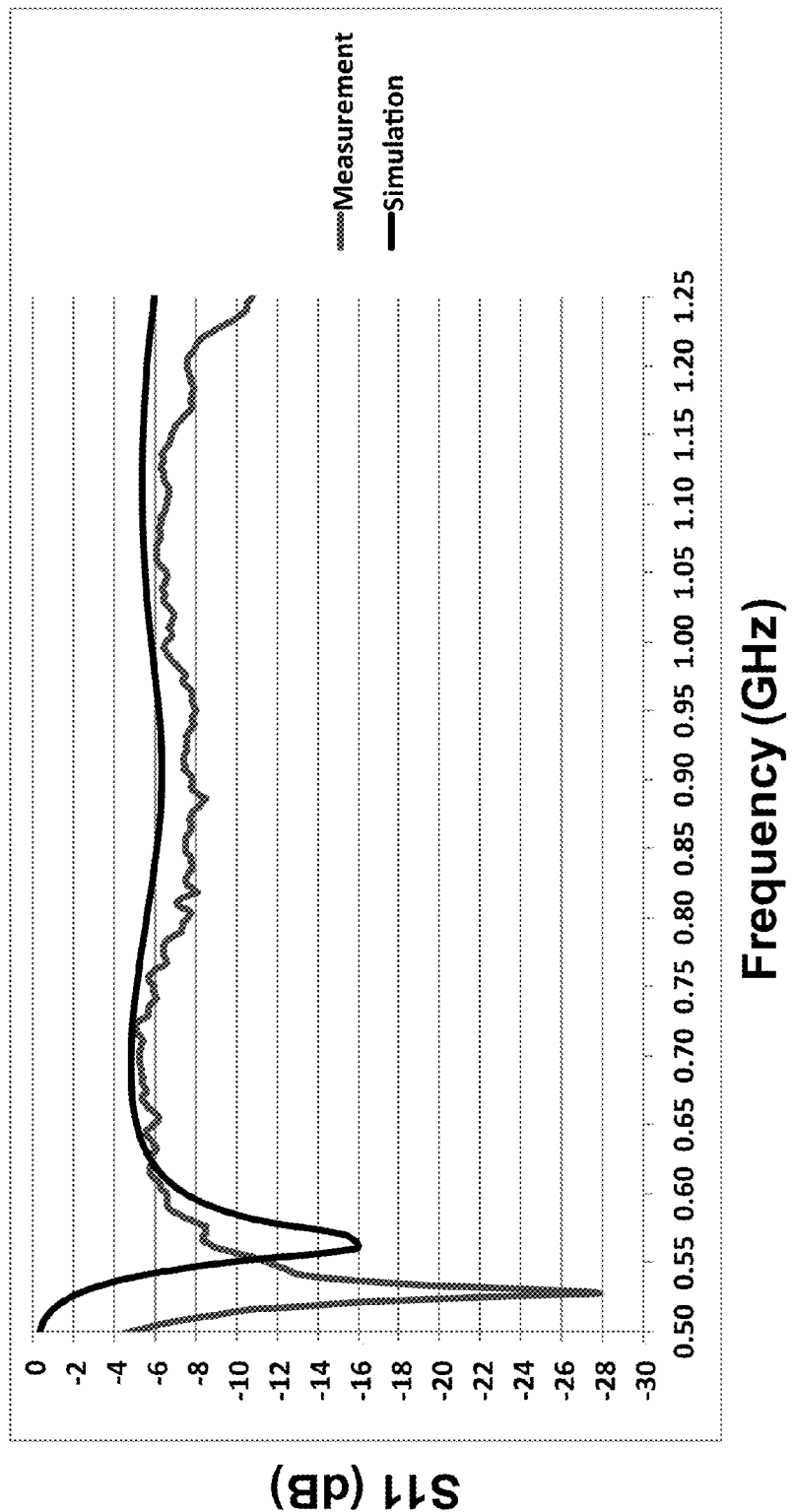
FIG. 7 shows an example of the return loss characteristics of the antenna assembly of FIGS. 6A-6C.

FIG. 7 illustrates the comparison of return loss over the frequency band of interest for the HFSS model (from the finite element solver) and the prototype of the antenna assembly of FIG. 6. The return loss characterizes the amount of reflected energy from impedance mismatching of the antenna. More reflection loss indicates a more effective power transfer. As shown in FIG. 7, both simulated and actually measured values for the return loss were generally less than or equal to −5 dB. The actually measured prototype values closely matched or improved upon the modeling results at frequencies between 500 MHz and 1.25 GHz.

Figure 8:
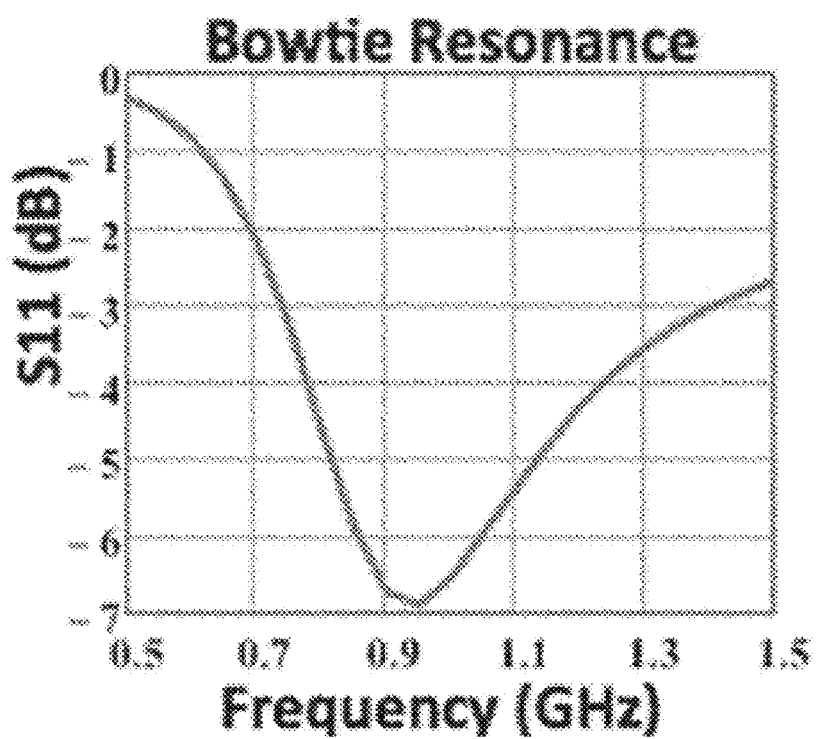
FIG. 8 shows an example of simulated return loss characteristics of an antenna assembly with a resonance at about 915 MHz.

FIG. 8 shows an example of simulated return loss characteristics of an antenna assembly designed with a resonance frequency of 915 MHz. As shown, a reflection notch occurs at 915 MHz as desired following the parameterizing of the bowtie antenna to 915 MHz.

Figure 9A:
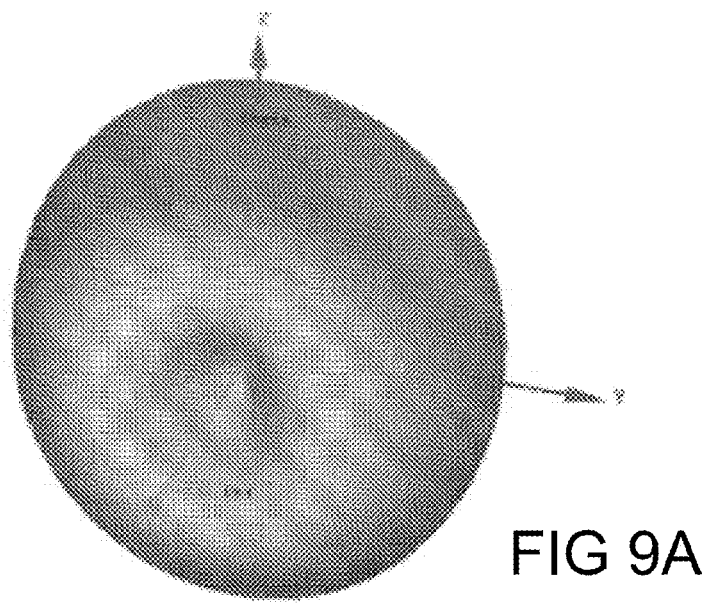
FIGS. 9A-9B show examples of simulated electromagnetic radiation patterns from the antenna assembly of FIG. 8.
Figure 9B:
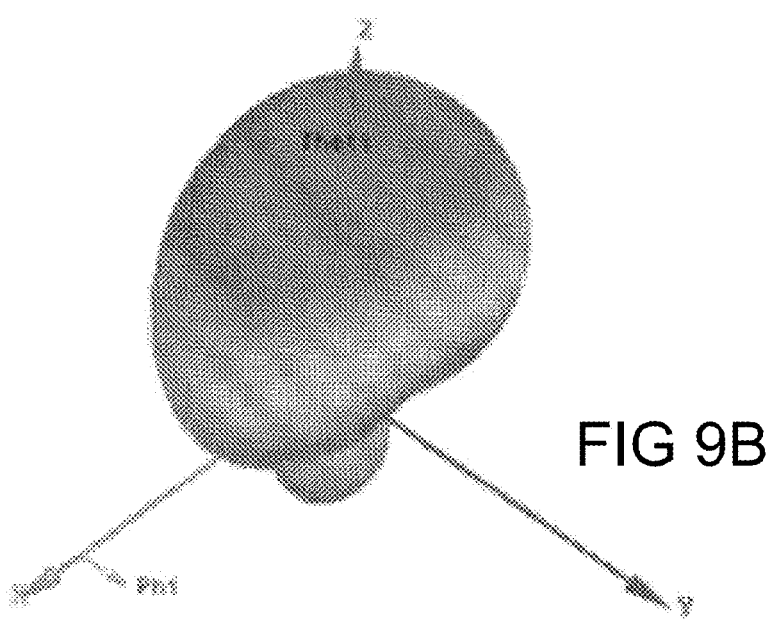

FIGS. 9A-9B show examples of simulated electromagnetic radiation patterns from the antenna assembly of FIG. 8. These patterns correspond to the total far field radiation pattern at resonance (915 MHz) for the parameterized bowtie antenna. In FIG. 9A, the pattern is calculated for the bowtie antenna and without a wave guide. In this arrangement, the bowtie antenna radiates uniformly around its axis of polarization. To improve directivity of the transmitting antenna 110, a rectangular waveguide can be placed around the bowtie antenna. FIG. 9B shows the improved directivity as demonstrated in the far field radiation pattern for the bowtie antenna at resonance (915 MHz) and with a rectangular aperture waveguide. As illustrated, the energy is concentrated in a lobe as directed by the aperture of the waveguide. Thus, adding the waveguide around the bowtie antenna significantly increases the antenna directivity as desired. In some cases, the beam width can be reduced by 50% or more by the rectangular waveguide. However, the return loss, and in turn the impedance match, may decrease due to frequency shaping caused by a cutoff frequency of the wave guide. To mitigate this down side, the mouth of the waveguide may be loaded with a tapered dielectric (e.g., Dk=3) dome.

Figure 10:
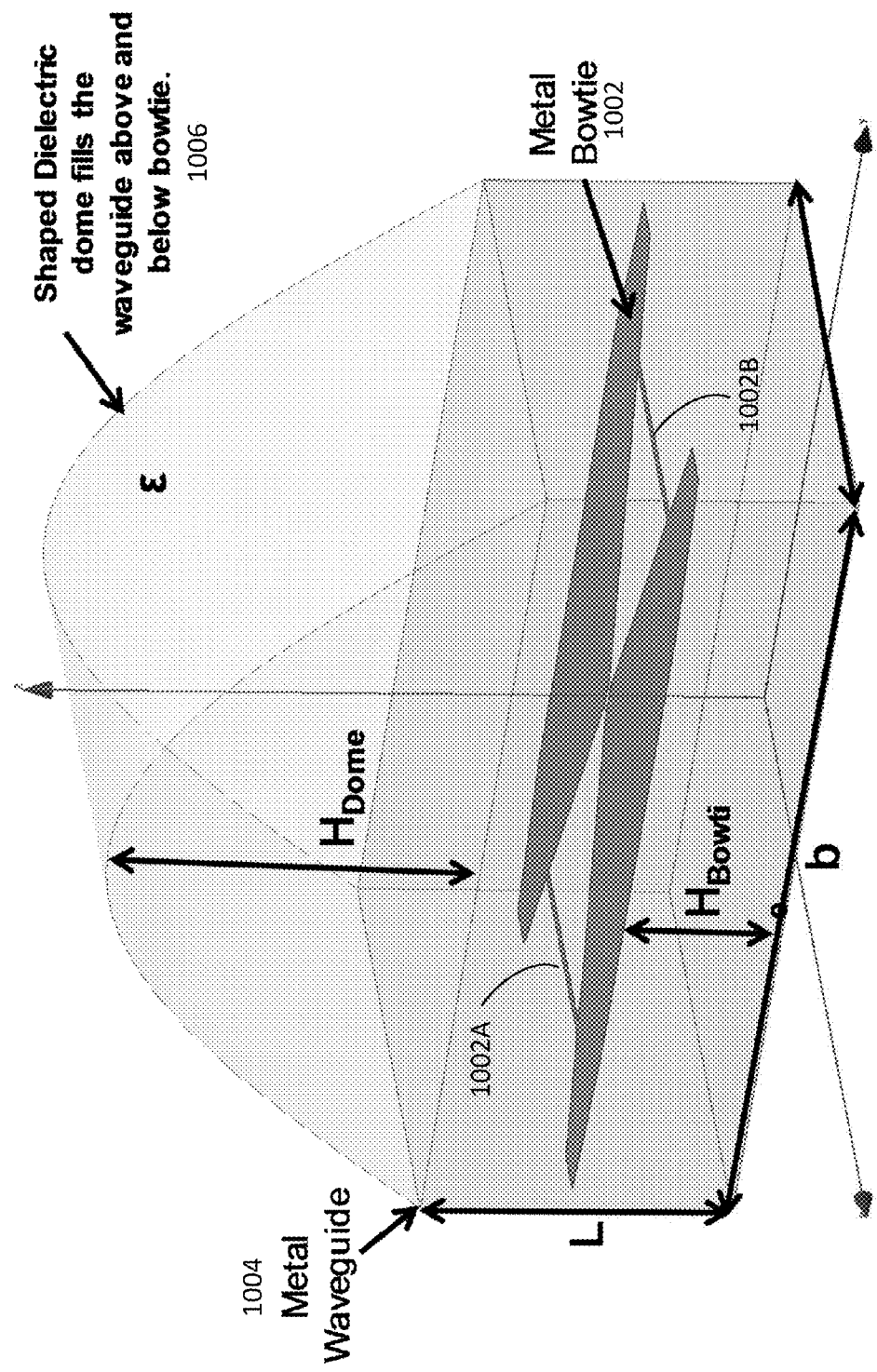
FIG. 10 illustrates an example of an antenna assembly including a bowtie-shaped radiating surface, a wave guide, and a dielectric lens.

Referring now to FIG. 10, a dielectric dome 1006 is mounted on the mouth of the waveguide aperture 1004 and over the radiating surface 1002. In this arrangement, the dome 1004 acts as a focusing lens at the mouth of the antenna. The addition of the dielectric dome 1006 to fill the wave guide and over the mouth of the wave guide can provide several benefits to the design of the bowtie antenna, including, for example, lowering the return loss cutoff frequency of the rectangular wave guide without the dielectric filling to below 915 MHz so that the size of the rectangular wave guide can be further reduced. Further, the dielectric dome, when tapered, can spatially narrow the energy transmitted so that the transmission becomes more focused. For example, the dielectric dome, tapered in one dimension, can cause the beam width of the radiated electromagnetic wave to be narrower in the same dimension.

The dome may be of a simple half-cycle sinusoid or Gaussian shape, for example, along the Y direction (while the profile along the X-direction may remain constant). As discussed above, the antenna assembly may induce a wave guide mode of transmission pattern that is polarized along the X direction (along the direction of the long axis of rod structures 1002A and 1002B). Notably, the shaped dielectric dome may fill the wave guide above and below the bowtie antenna. Yet, the shape or profile variation extends only from the mouth of the wave guide, as illustrated. The shape or profile variation— along the Y direction as illustrated in this case—may facilitate reducing the spread of the transmitted electromagnetic energy as it propagates forward.

The height of the dome—Hdome—can be configured to improve S11 (return loss) and S21 (transmission loss). The height of dome refers to the height extending from the month of the wave guide to the summit of the dome. In some implementations, the height may vary from 0.5 in to 6 in, depending on the dielectric constant, which can vary from 1.5 to 9. For a 915 MHz operation, the height of the dielectric dome was chosen at 3 inches.

As illustrated, L denotes the length of the wave guide and scales in the range from 2.5 cm to 10 cm. Hbowtie refers to the height position of the Bowtie and may be fixed at L/2. In this illustration, "a" refers to the shorter lateral dimension of wave guide base, which can scale in the range from 3.75 cm to 7.5 cm, while "b" refers to the longer lateral dimension of the wave guide base, which may range from 7.5 cm to 15 cm. Choosing a particular dielectric constant may reduce the size of the wave guide. The dielectric constant may also help release the electromagnetic wave from the metal wave guide, thereby serving as a buffer to reduce the reflection at the feed port. The feed port may be coupled to a 50 ohm coaxial cable via various connectors (e.g., BNC, SMA, etc.) as discussed above.

Figure 11A:
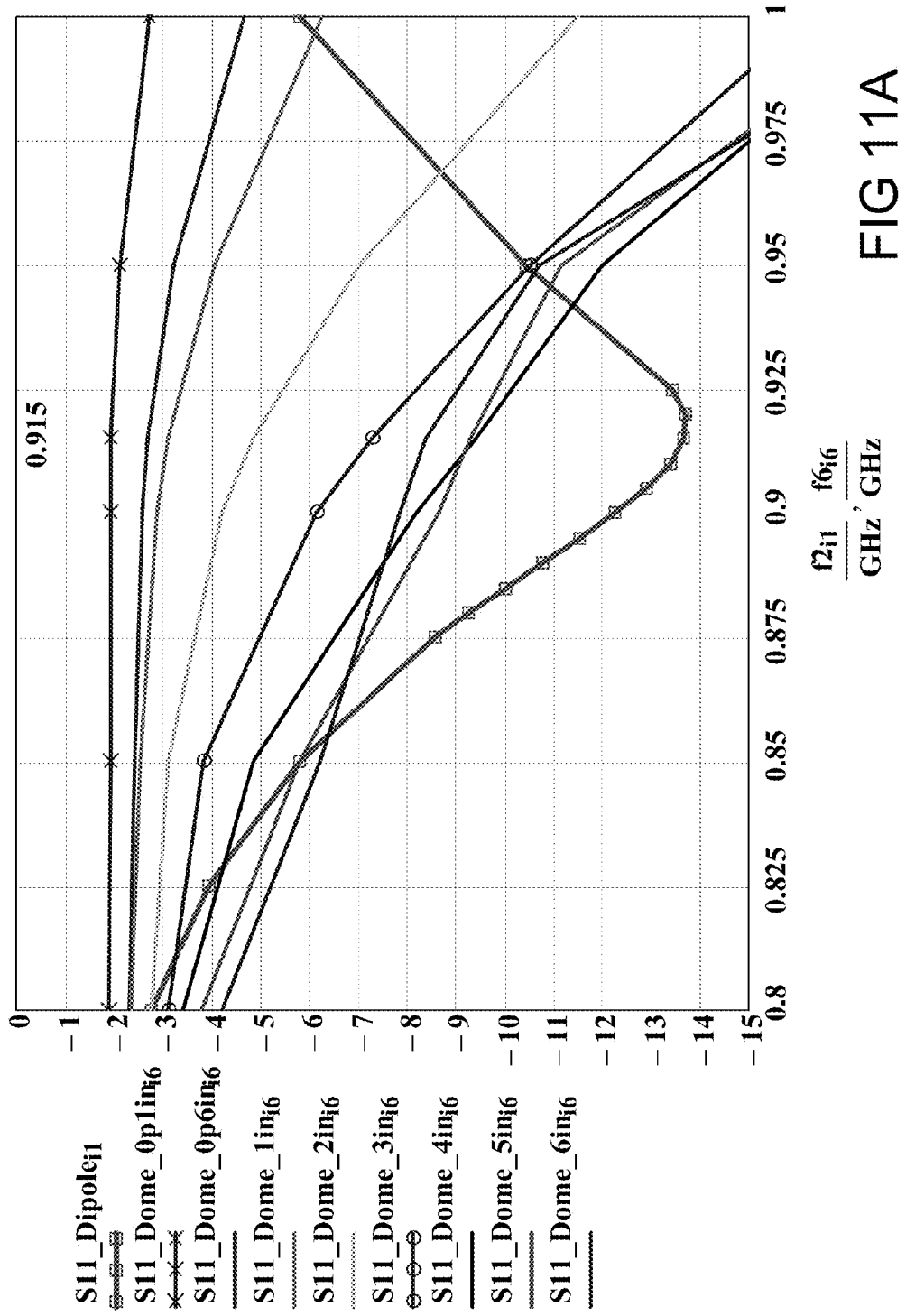
FIGS. 11A-11B shows the simulated return loss and transmission characteristics of the antenna assembly of FIG. 10.
Figure 11B:
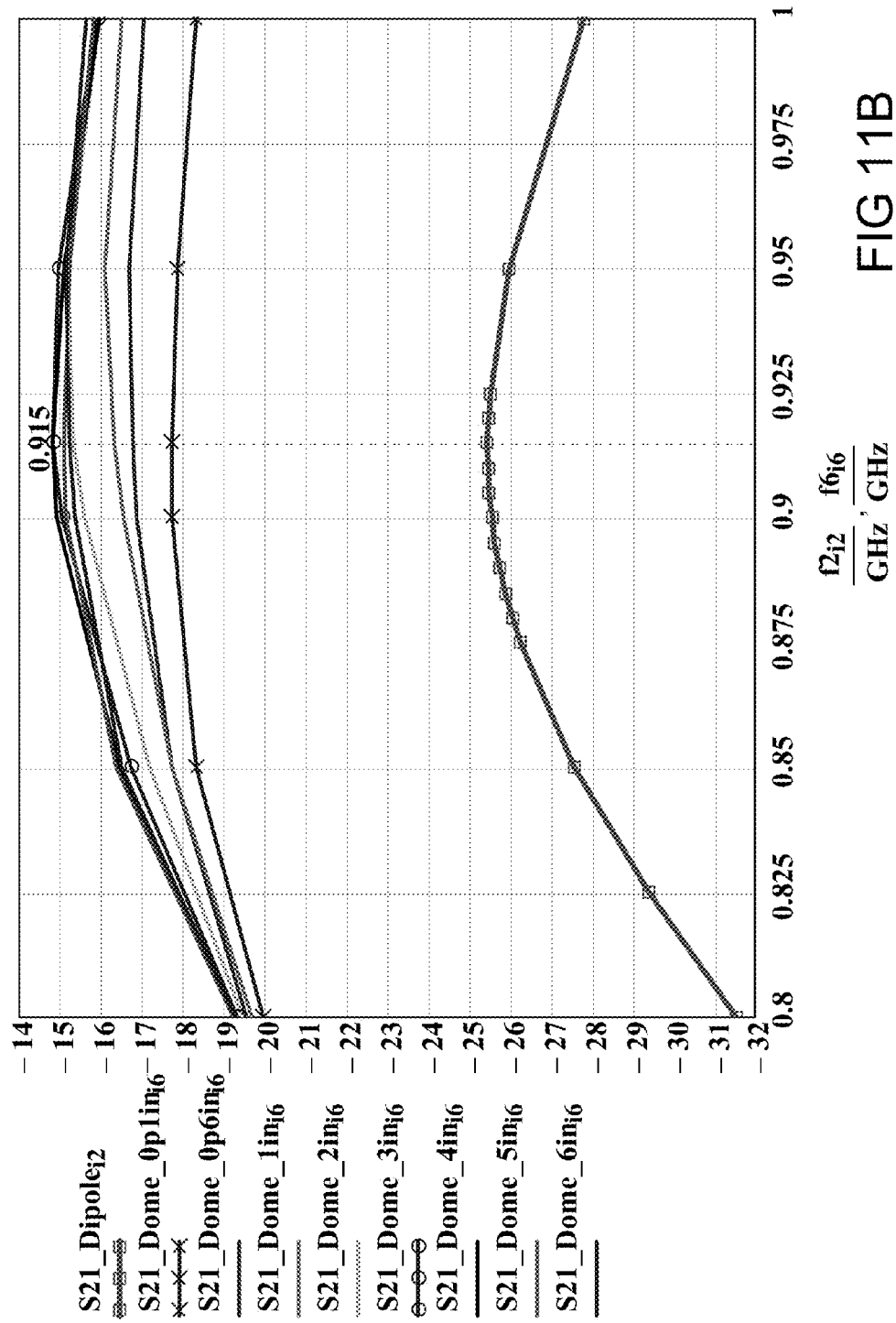

FIGS. 11A-11B shows the simulated return loss and transmission characteristics of the antenna assembly of FIG. 10. In FIG. 11A, the return loss is plotted as a function of frequency, for a range of dome heights. In particular, the return loss shown is a relative return loss, as compared to a baseline return loss for two dipole antennas operating at 915 MHz and separated at 1 in apart. The results from the parameterizations (i.e., designing by adjusting system parameters) show that a dome height of three inches and greater produce good matches. However, the size trade-offs for the relatively small gains in reflection loss indicate only marginal gains above three inches. Thus, three inches may be deemed as the smallest height with an acceptable reflection loss, and thus the desirable dome height.

FIG. 11B shows the simulated transmission loss versus frequency for a range of dome heights. Transmission loss is a characterization of the attenuation of the transmitted electromagnetic wave. Larger values (less negative values) correspond to a better transmission loss and a more efficient antenna. Gains in transmission loss are diminishing when the dome height is over three inches. Notably, the transmission loss may serve as a complimentary measure of the performance of the remote transmission antenna. Thus, little benefit may be derived from making the dome height larger than three inches.

Following this parameterization, the dimensions can be judiciously determined. An example of dimensions for 915 MHz are presented in Table 2. The reflection and transmission loss plots illustrate that the design is substantially improved for the purpose of this disclosure, but to further validate the results, the contours of the electric field interactions at the receiver and the far field radiation pattern can be examined. The waveguide dimensions shown below in Table 2 scale with the dimensions of the bowtie antenna (as shown above in Table 1).

TABLE 2

Final remote antenna dimensions following parameterization

| Optimized Remote Antenna Dimension | Value [units] |
|---|---|
| Length of the Waveguide (Interior) | 15.0 [cm] |
| Width of the Waveguide (Interior) | 7.6 [cm] |
| Height of the Waveguide (Interior) | 5.0 [cm] |

Figure 12:
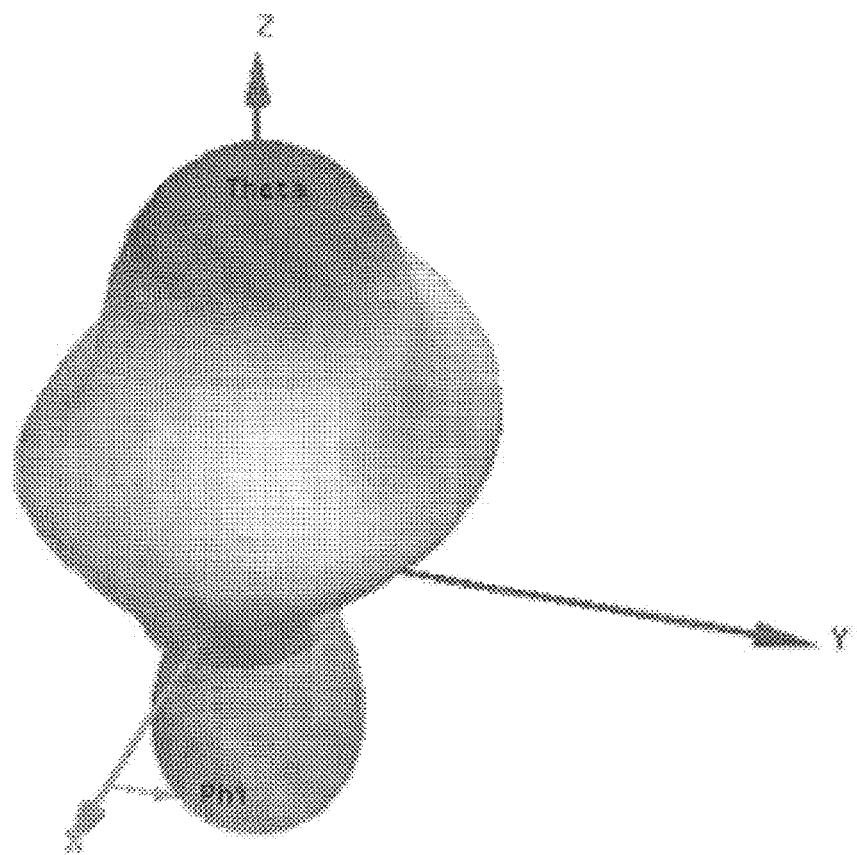
FIG. 12 shows the perspective view of the simulated electromagnetic radiation pattern from the antenna assembly of FIG. 10.

FIG. 12 shows the perspective view of the simulated electromagnetic radiation pattern from the antenna assembly of FIG. 10. In particular, FIG. 12 shows the far field radiation pattern at 915 MHz for the remote antenna design according to Table 2. The dielectrically loaded waveguide further improves directivity of the antenna to provide sufficient energy for delivery to the implanted neural stimulator device. The far field pattern shows that the additional dielectric loading further improves directivity that validates the previously found loss characterizations as well as the E-field propagation results. Additionally, the pattern quantifies the spatial orientation variability of the antenna with respect to the implanted neural stimulator device. The results demonstrate that the implanted neural stimulator can be within 15° of the center axis of the remote transmitting antenna and still receive the majority of the transmitted energy.

Figure 13B:
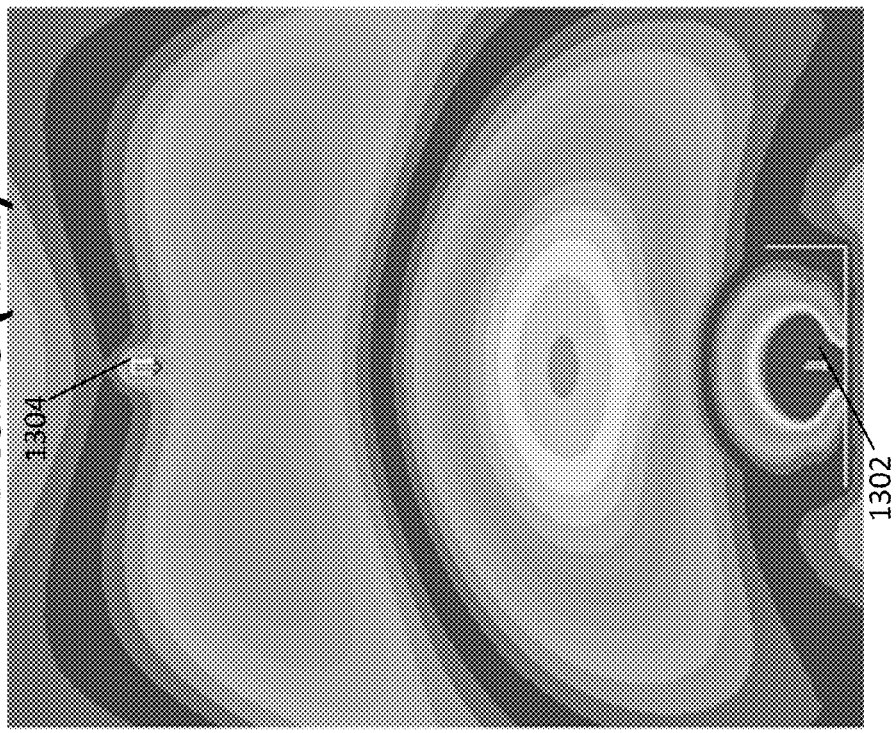
FIG. 13A-13B shows the X-Z and Y-Z plane view of the simulated electromagnetic radiation pattern of FIG. 12.
Figure 13A:
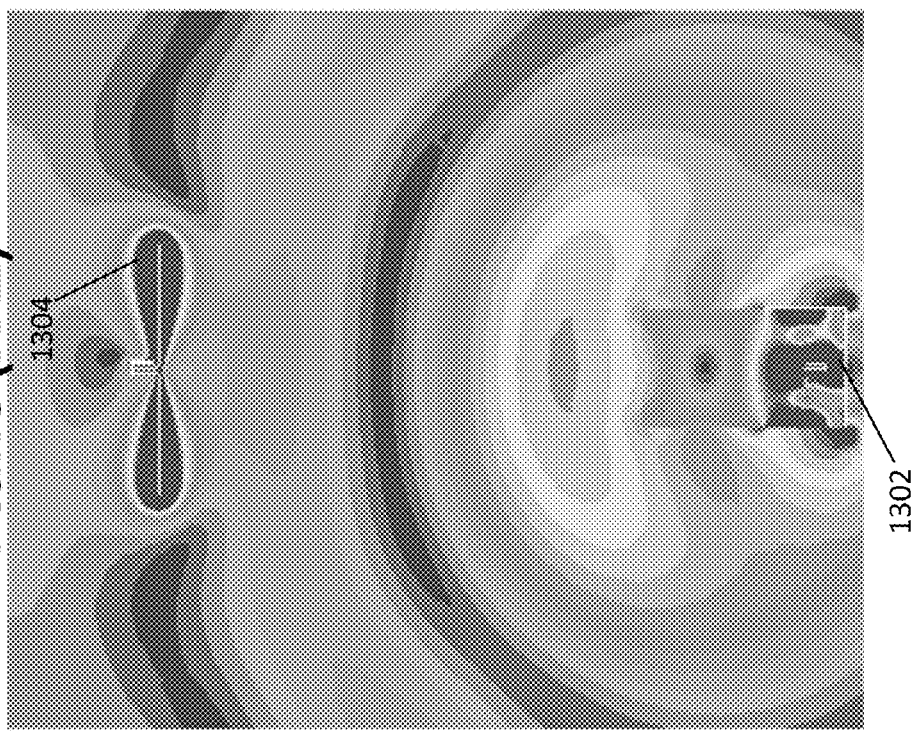

FIG. 13A-13B shows the X-Z and Y-Z plane views of the simulated electromagnetic radiation pattern of FIG. 12. The receiver antenna 1304 is in the top portion of both planes. The contours show a forward traveling lobe of electromagnetic energy interacting with the receiver antenna 1304. These graphs show that the transmitting antenna 1302 and the receiver antenna 1304 couple together well because the transmitting antenna 1302 is directive to the implant that includes receiver antenna 1304, and that energy is efficiently delivered to the implant. The far field radiation pattern at 915 MHz improves due to the further parameterizations performed, as discussed above.

A number of implementations have been described. Nevertheless, it will be understood that various modifications may be made. Accordingly, other implementations are within the scope of the following claims.

What is claimed is:

1. An antenna assembly, comprising:
an antenna that includes:
a metal signal layer having a radiating surface; and
a feed port; and
a waveguide surrounding the antenna and configured to guide electromagnetic energy transmitted from the radiating surface in a direction away from the antenna; and
a controller module connected to the feed port and configured to drive the antenna to transmit electromagnetic energy from the radiating surface;
wherein the radiating surface is bowtie shaped and has two leaf structures connecting to each other at the feed port as well as through two substantially parallel rod structures, and wherein the antenna, waveguide, and controller module are configured such that, when the controller module drives the antenna, the transmitted electromagnetic energy matches a reception characteristic of an implantable device and is sufficient for the implantable device to create one or more electrical pulses of sufficient amplitude to stimulate neural tissue of a patient, solely using electromagnetic energy received from the antenna, when the implantable device is located at least 10 centimeters away from the antenna.

2. The antenna assembly of claim 1, further comprising:
a dielectric lens that fills the wave guide and protrude outward from an opening of the wave guide to form a protrusion that is shaped to spatially narrow the transmitted electromagnetic energy in the direction away from the transmitting surface.

3. The antenna assembly of claim 2, wherein the protrusion is tapered in shape.

4. The antenna assembly of claim 3, wherein the protrusion is tapered to have a Gaussian or sinusoid profile.

5. The antenna assembly of claim 3, wherein the antenna assembly has a return loss cutoff frequency associated with the wave guide and the dielectric lens is further configured to lower the return loss cutoff frequency.

6. The antenna assembly of claim 1, wherein the antenna is operable within a frequency band from about 500 MHz to about 4 GHz.

7. The antenna assembly of claim 1, wherein the transmitted electromagnetic energy is polarized along a long axis of the rod structures.

8. The antenna assembly of claim 1, wherein the radiating surface is adjustable from a first spatial orientation to a second spatial orientation such that polarized electromagnetic energy received at the implantable device is increased.

9. The antenna assembly of claim 1, wherein the waveguide is a rectangular waveguide having four walls that surround the bowtie shaped radiating surface.

10. The antenna assembly of claim 9, wherein the rectangular waveguide has an interior length of about 15 cm, an interior width of about 7.6 cm, and a height of about 5 cm.

11. The antenna assembly of claim 9, wherein the rectangular waveguide has an interior length of at least 10 cm, and the rectangular waveguide has an interior length, width, and height ratio of about 15:7.6:5.

12. A method for wirelessly supplying energy to an implantable device, the method comprising:
radiating electromagnetic energy from a radiating surface on an antenna assembly, the radiated electromagnetic energy reaching an implantable device located at least 10 centimeters away and implanted inside a patient such that the implantable device creates, solely by using the radiated electromagnetic energy, one or more electrical stimulation pulses suitable for stimulating neural tissue of the patient, and applies the electrical stimulation pulses to neural tissue of the patient, wherein radiating the electromagnetic energy further comprises radiating the electromagnetic energy while the patient is asleep such that the created one or more electrical simulation pulses is applied to stimulate the patient's neural tissue during the patient's sleep.

13. The method of claim 12, further comprising: adjusting a position of the antenna assembly such that the radiating surface of the antenna assembly is no more than six feet from the implantable device.

14. The method of claim 12, further comprising: adjusting a position of the antenna assembly such that the radiating surface of the antenna assembly is no less than one foot from the implantable device.

15. The method of claim 12, further comprising: adjusting an orientation of the antenna assembly such that the radiated electromagnetic energy received at the implantable device is increased.

16. The method of claim 12, further comprising:
connecting the antenna assembly to a controller module; and
driving the antenna assembly from the controller module connected thereto such that the radiating surface on the antenna assembly radiates electromagnetic energy to power the implantable.

17. The method of claim 16, further comprising:
establishing a link between a programming module to the controller module; and
transmitting, from the programming module to the controller module, data encoding parameters of the one or more stimulation pulses to be created at the implantable device and to be subsequently applied to stimulate the patient's neural tissue.

18. A system, comprising:
an antenna assembly that wirelessly powers an implantable device, the antenna assembly including:
an antenna that includes:
a metal signal layer having a radiating surface and configured to transmit electromagnetic energy via radiative coupling;
a waveguide surrounding the antenna and configured to guide electromagnetic energy transmitted from the radiating surface in a direction away from the antenna; and;
a controller module connected to the feed port of the antenna and configured to drive the antenna assembly such that the radiating surface on the antenna radiates electromagnetic energy,
wherein the radiating surface is bowtie shaped and has two leaf structures connecting to each other at the feed port as well as through two substantially parallel rod structures.

19. The system of claim 18, further comprising:
an implantable operable from a location inside a patient and more than 10 centimeters away from the antenna assembly,
wherein the implantable device creates one or more stimulation pulses of sufficient amplitude to stimulate neural tissue of the patient solely using electromagnetic energy received from the antenna assembly.

20. The system of claim 18, wherein the waveguide is a rectangular waveguide having four walls that surround the radiating surface.

21. The system of claim 20, wherein the rectangular waveguide has an interior length of about 15 cm, an interior width of about 7.6 cm, and a height of about 5 cm.

22. The system of claim 20, wherein the rectangular waveguide has an interior length of at least 10 cm, and the rectangular waveguide has an interior length, width, and height ratio of about 15:7.6:5.

23. The system of claim 18, further comprising:
a dielectric lens that fills the wave guide and protrude outward from an opening of the wave guide to form a protrusion that is shaped to spatially narrow the transmitted electromagnetic energy in the direction away from the transmitting surface.

24. The system of claim 23, wherein the protrusion is tapered in shape.

25. The system of claim 24, wherein the protrusion is tapered to have a Gaussian or sinusoid profile.

26. The system of claim 18, wherein the antenna is operable within a frequency band from about 500 MHz to about 4 GHz.

27. The system of claim 18, wherein the transmitted electromagnetic energy is polarized along a long axis of the rod structures.

28. The system of claim 18, wherein the implantable device includes a dipole antenna located on the implantable device inside the patient, and the radiating surface is adjustable from a first spatial orientation to a second spatial orientation such that polarized electromagnetic energy received at the dipole antenna is increased.

* * * * *